US008831776B2

(12) United States Patent (10) Patent No.: US 8,831,776 B2
Lefebvre et al. (45) Date of Patent: Sep. 9, 2014

(54) INTEGRATED TISSUE PROCESSING AND EMBEDDING SYSTEMS, AND METHODS THEREOF

(75) Inventors: Gilles Lefebvre, San Clemente, CA (US); Robert E. Evans, Pasadena, CA (US)

(73) Assignee: Sakura Finetek U.S.A., Inc., Torrance, CA (US)

( * ) Notice: Subject to any disclaimer, the term of this patent is extended or adjusted under 35 U.S.C. 154(b) by 957 days.

(21) Appl. No.: 12/549,313

(22) Filed: Aug. 27, 2009

(65) Prior Publication Data

US 2011/0054679 A1 Mar. 3, 2011

(51) Int. Cl.
*G06F 19/00* (2011.01)
*G05B 19/18* (2006.01)
*G01N 1/36* (2006.01)

(52) U.S. Cl.
CPC .................................. *G01N 1/36* (2013.01)
USPC .............................. 700/245; 435/40.5

(58) Field of Classification Search
CPC .................. B01J 2208/00008; G01N 1/30
USPC .......... 700/61, 245, 266; 435/40.5, 283.1, 325
See application file for complete search history.

(56) References Cited

U.S. PATENT DOCUMENTS

| 3,807,353 | A | * | 4/1974 | Kobernick | 118/702 |
|---|---|---|---|---|---|
| 4,802,377 | A | | 2/1989 | Keppler | |
| 6,821,072 | B2 | | 11/2004 | Thiem et al. | |
| 7,470,401 | B2 | | 12/2008 | Morales | |
| 2001/0051365 | A1 | * | 12/2001 | Morales et al. | 435/173.4 |
| 2003/0026738 | A1 | * | 2/2003 | Everett | 422/102 |
| 2008/0199955 | A1 | * | 8/2008 | Ulbrich et al. | 435/325 |

OTHER PUBLICATIONS

"Histotechniques", http://library.med.utah.edu/WebPath/HISTHTML/HISTOTCH/HISTOTCH.html, (Mar. 25, 2009), 11 pages.
Sakura Finetek U.S.A., Inc., "The New Era in Rapid Tissue Processing", *Tissue-Tek® Xpress® x Series*, (2007), 4 pages.
Sakura Finetek U.S.A., Inc., "A Career to Consider: The Art and Science of Histotechnology", (2001), 12 pages.
Sakura Finetek U.S.A., Inc., "Placing productivity in a new light", *Tissue-Tek® Paraform®; Sectionable Cassett, System*, (2004), 8 pages.
Sakura Finetek U.S.A., Inc., "Tissue-Tek® TEC™ 5", *Tissue Embedding Console System*, Advance Features, More Performance, (2003), 3 pages.
Sakura Finetek U.S.A., Inc., "Tissue-Tek® VIP™ 5", *Vacuum Infiltration Processor*, The Evolution of Reliability, (2003), 4 pages.
Sakura Finetek U.S.A., Inc., "Tissue-Tek® AutoTEC® Automated Embedding System", http://www.sakura-americas.com/products/tisstek-autotec.html, (Sep. 11, 2008), 6 pages.

\* cited by examiner

*Primary Examiner* — Mary Cheung
(74) *Attorney, Agent, or Firm* — Blakely Sokoloff Taylor & Zafman LLP

(57) ABSTRACT

Apparatus and methods for integrating tissue processors and embedding systems. An apparatus, of one aspect, includes a robot. The robot has a work envelope that encompasses a location having a tissue holder and an input of an embedding system. The tissue holder has at least one processed tissue. The robot is configured to transfer the tissue holder from the location to the input of the embedding system. A method, of one aspect, may include moving a robot to a location having a tissue holder. The tissue holder may have at least one processed tissue. The robot may engage with the tissue holder at the location. The robot may move the tissue holder from the location to an input to an embedding system. The robot may disengage from the tissue holder at the input to the embedding system. Other methods, apparatus, and systems are also disclosed.

18 Claims, 15 Drawing Sheets

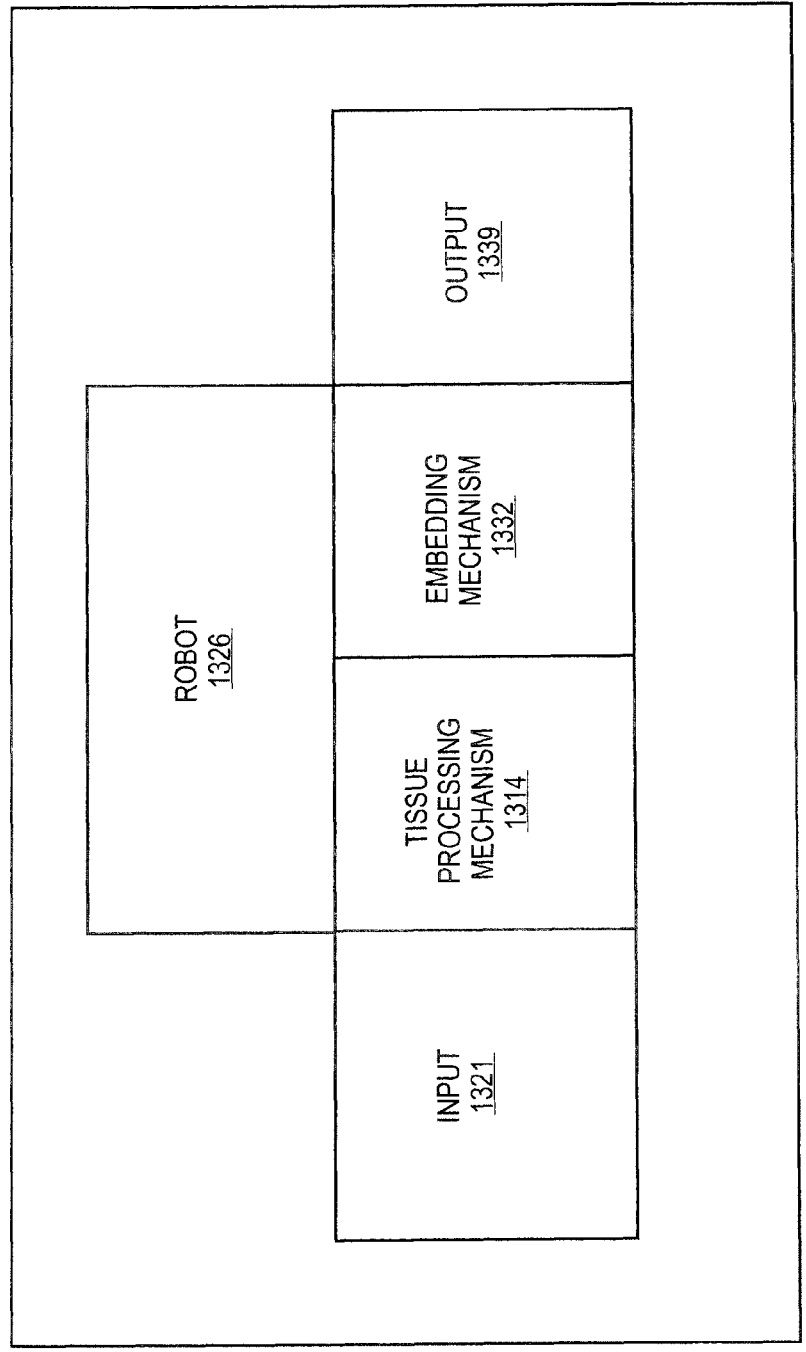

INTEGRATED TISSUE PROCESSING AND EMBEDDING SYSTEMS, AND METHODS THEREOF

BACKGROUND

1. Field

Integrated tissue processing and embedding systems, and methods.

2. Background Information

Histology is a science or discipline associated with the processing of tissue for examination or analysis. The examination or analysis may be of the cellular morphology, chemical composition, tissue structure or composition, or other tissue characteristics. Histology is used in research, diagnostic, and other applications.

FIG. 1 is a block flow diagram of an embodiment of histological method 100. This is just one representative histological method. Various modifications of this histological method exist, such as by adding, removing, and/or rearranging operations.

At block 101, grossing and fixation may be performed on tissue. The tissue may represent tissue samples or specimens taken during biopsies, autopsies, surgeries, or other tissue extractions. The tissue may also represent a pellet of tissue. Grossing the tissue may potentially include examining the tissue, describing the tissue, and trimming the tissue to an appropriate size and/or shape. Fixing or fixating the tissue may include placing the grossed tissue in a fixative solution, which may help to preserve the tissue and/or prevent decomposition.

After grossing and fixation, tissue processing may be performed on the tissue, at block 102. During tissue processing, the tissue may be dried or dehydrated by removing most or almost all of the water from the tissue. Commonly, such drying may be achieved by exposing the tissue to one or more dehydrating agents. After drying the tissue, clearing of the dehydrating agents may optionally be performed, and then wax (e.g., paraffin), wax with added plasticizers, or another embedding agent may be introduced or infiltrated into the dried tissue. In some cases, a vacuum may be applied to assist with infiltration of the wax or other embedding agent into the tissue.

As will be explained further below, it is common in histology to cut the tissue into a thin section, for example with a microtome. Cutting a tissue that has not undergone tissue processing may tend to be challenging. Without tissue processing, the tissue may be soft and filled with water. Force exerted on the tissue by a blade that is used to cut the tissue into the thin sections may tend to compress the tissue and force some of the water out of the tissue. The tissue may not fully decompress after removal of the blade. This may tend to alter the structure of the tissue, which in some cases may tend to hinder examination or analysis. However, removing the water from the tissue, and infiltrating wax or another embedding agent into the tissue (e.g., infiltrating into interstices of the tissue), may help to allow the tissue to be cut with less compression and/or alteration of the tissue structure.

After tissue processing, embedding may be performed on the tissue, at block 103. During embedding, the tissue that has been dried and infiltrated with wax or another embedding agent during tissue processing may be embedded in a block or other mass of wax, various polymers, or another embedding medium. Representatively, the dried and wax-infiltrated tissue may be placed in a mold, melted wax may be dispensed over the tissue until the mold has been filled with the wax, and then the wax may be cooled and hardened. Embedding the tissue in the block of wax may help to provide additional support during cutting or sectioning of the tissue.

After embedding, the tissue embedded in the block of wax may be sectioned into thin tissue sections, at block 104. During sectioning a microtome or other bladed instrument may be used to cut the tissue embedded in the block of wax into the thin sections. By way of example, the thickness of the tissue sections may range from about one to ten microns. The sections, or a ribbon of multiple sequentially cut sections, may be floated on warm water, or otherwise softened and flattened, and then placed on microscope slides and allowed to dry.

After sectioning, the wax is removed and the thin tissue sections may be stained, at block 105. During staining, the tissue sections may be exposed to various stains. The stains may combine with the tissue sections to provide contrast between tissue components, structures, molecules, or some combination thereof, depending upon the particular stains. Some stains combine non-specifically chemically with the tissue, whereas other stains combine specifically with certain bacteria types, enzymes, molecules, portions of molecules, etc.

After staining, coverslipping may be performed, at block 106. During coverslipping, a protective transparent cover may be applied over the stained tissue section. Coverslipping may aid in microscopic evaluation and/or may help to protect the tissue section from exposure to air and subsequent handling.

Currently, tissue processing is often performed automatically by an instrument known as an automated tissue processor. Likewise, embedding is often performed automatically by an instrument known as an automated embedding system. However, the automated tissue processor and the automated embedding system are currently separate, unconnected instruments.

Accordingly, after tissue processing has been performed, the tissue that has been dried and infiltrated with wax or another embedding agent needs to be manually removed from the automated tissue processor, moved to, and introduced into the automated embedding system before embedding may begin. Despite the automation within each of the separate instruments, manual unloading, transfer, and loading of tissue from the automated tissue processor to the automated embedding system is necessary.

Performing such operations manually tends to unnecessarily occupy the time of laboratory personnel, often at short intervals. This may tend to prevent or compete with the personnel performing other possibly more valuable services. In addition, due to other tasks, the personnel may not always transfer tissue from one instrument to the other as soon as possible, which may potentially lead to instrument downtime, and reduced productivity or throughput.

BRIEF DESCRIPTION OF THE SEVERAL VIEWS OF THE DRAWINGS

The invention may best be understood by referring to the following description and accompanying drawings that are used to illustrate embodiments. In the drawings:

FIG. 13 is a diagram of a seventh embodiment of an even more highly integrated tissue processing and embedding system.

DETAILED DESCRIPTION

Figure 1:
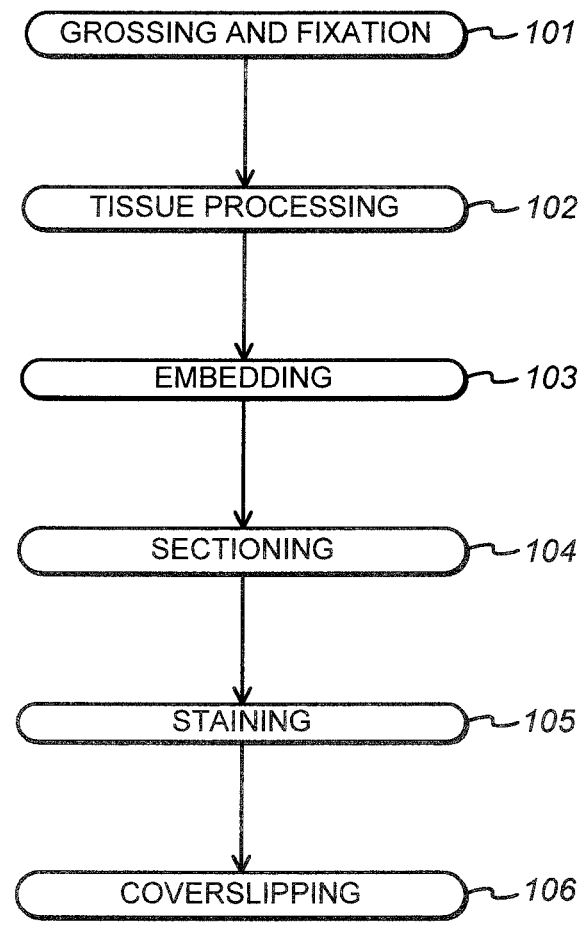
FIG. 1 is a block flow diagram of an embodiment of a histological method.
Figure 2:
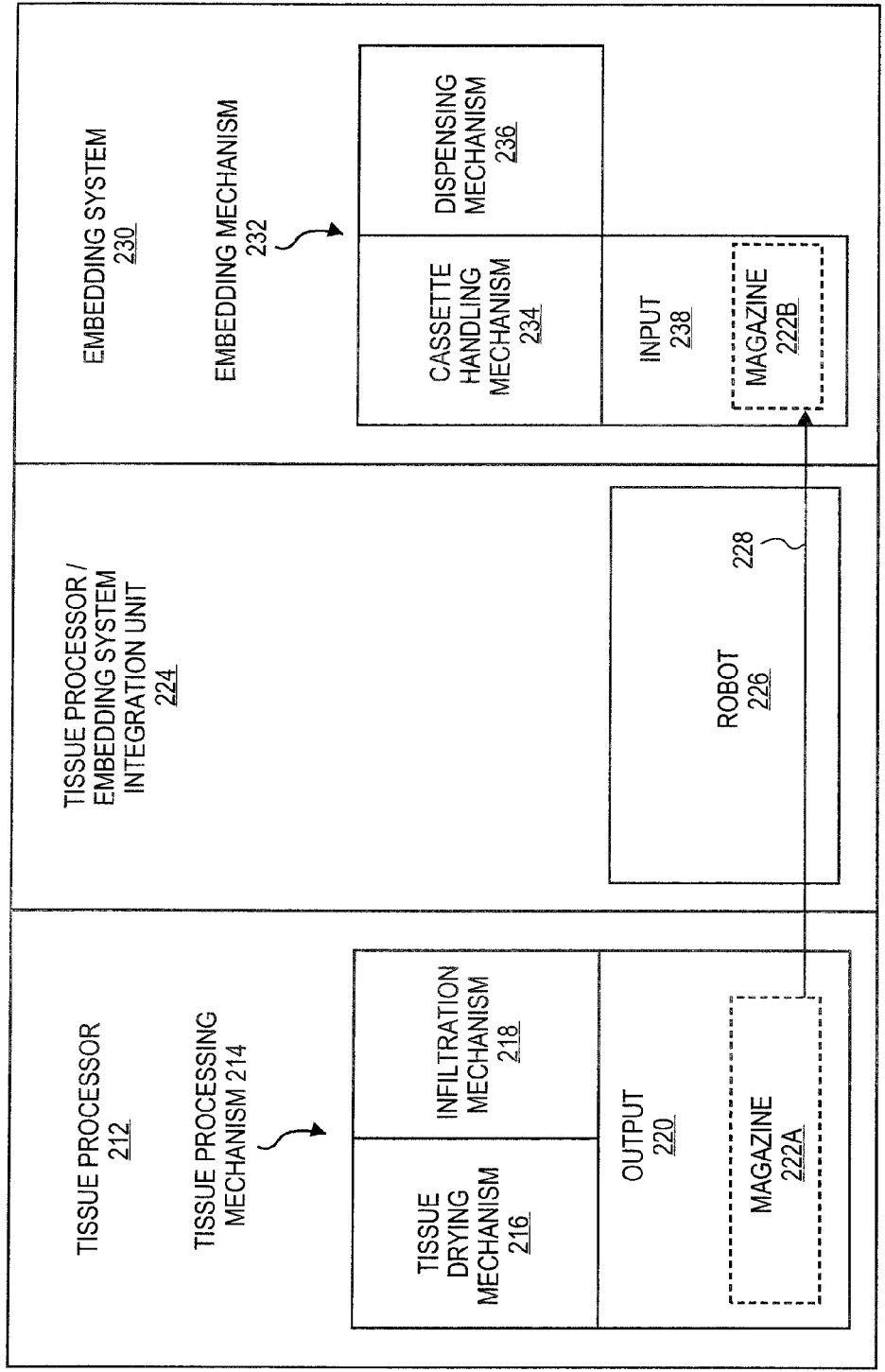
FIG. 2 is a block diagram of a first embodiment of an integrated tissue processing and embedding system.

FIG. 2 is a block diagram of a first embodiment of integrated tissue processing and embedding system 210. For convenience, the integrated tissue processing and embedding system may be referred to simply as an integrated system.

The integrated system includes tissue processor 212, embedding system 230, and tissue processor/embedding system integration unit 224. The tissue processor and the embedding system may perform their individual functions according to known instruments. As such, a detailed understanding of the inner mechanisms or workings of the tissue processor and the embedding system are not necessary. Accordingly, only a brief description will be provided.

Initially, a magazine having multiple cassettes, for example, may be input into the tissue processor through an input (not shown). Each of the cassettes may have a tissue, which has potentially been grossed and/or fixated.

Figure 3:
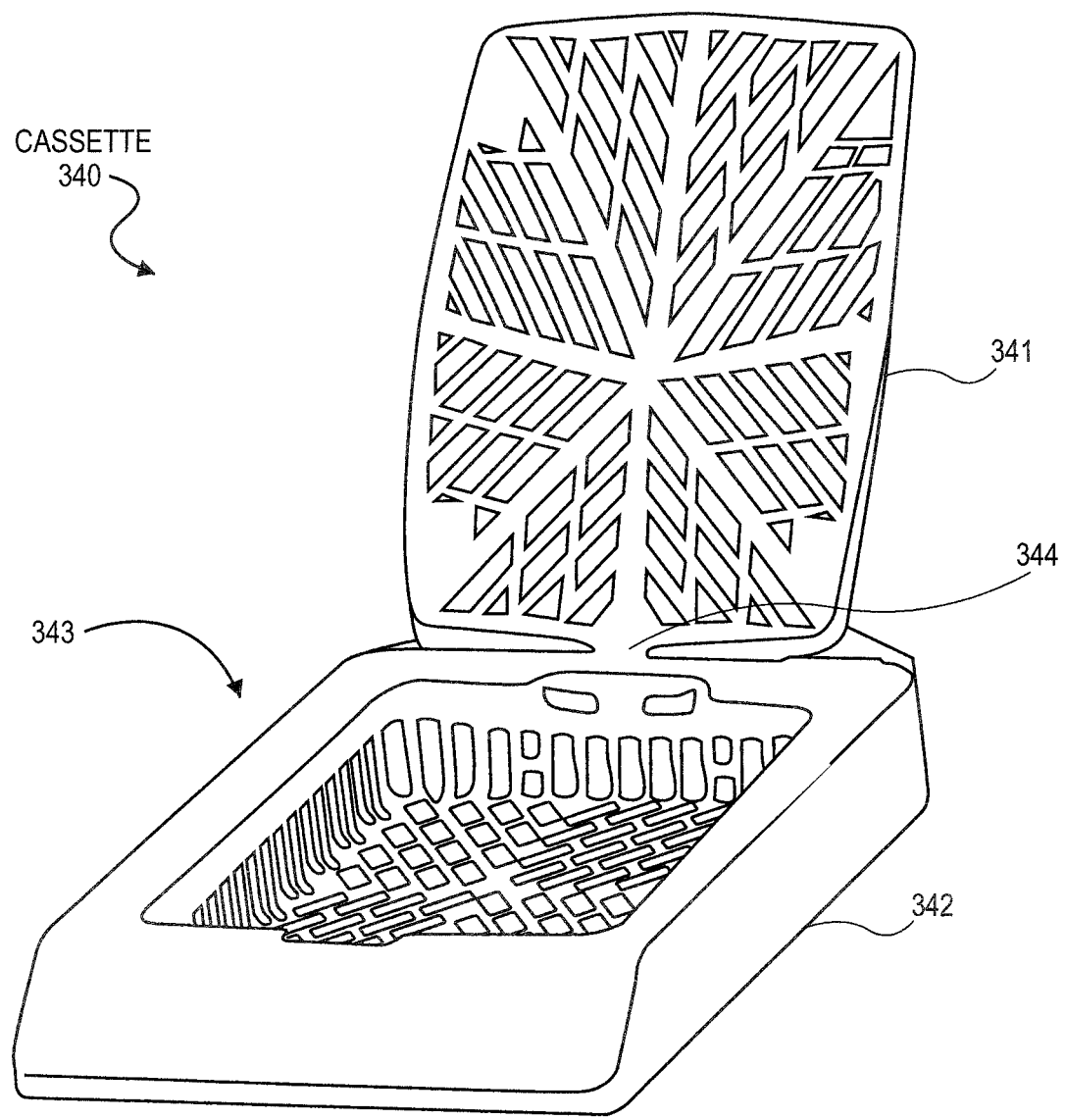
FIG. 3 is a representative embodiment of a tissue cassette.

FIG. 3 is a representative embodiment of cassette 340 which is suitable. In this embodiment, cassette 340 is a clam shaped cassette having top 341 and bottom 342 joined by hinge or other joint 344. The cassette may be opened to receive a tissue within compartment 343, and then the cassette may be closed around the tissue. As shown, the cassette may have an open structure defining a number of slits, holes, perforations, or other openings. These openings may allow access to the tissue by liquids, such as dehydrants, liquid wax, and the like. In one or more embodiments, the cassette may include a TISSUE-TEK® PARAFORM® brand sectionable cassette system having a unique PARAFORM® material, which is commercially available from Sakura Finetek USA, Inc., of Torrance, Calif. The PARAFORM® material allows sectioning directly through the cassette. Alternatively, various other commercially available cassettes are also suitable.

Figure 4:
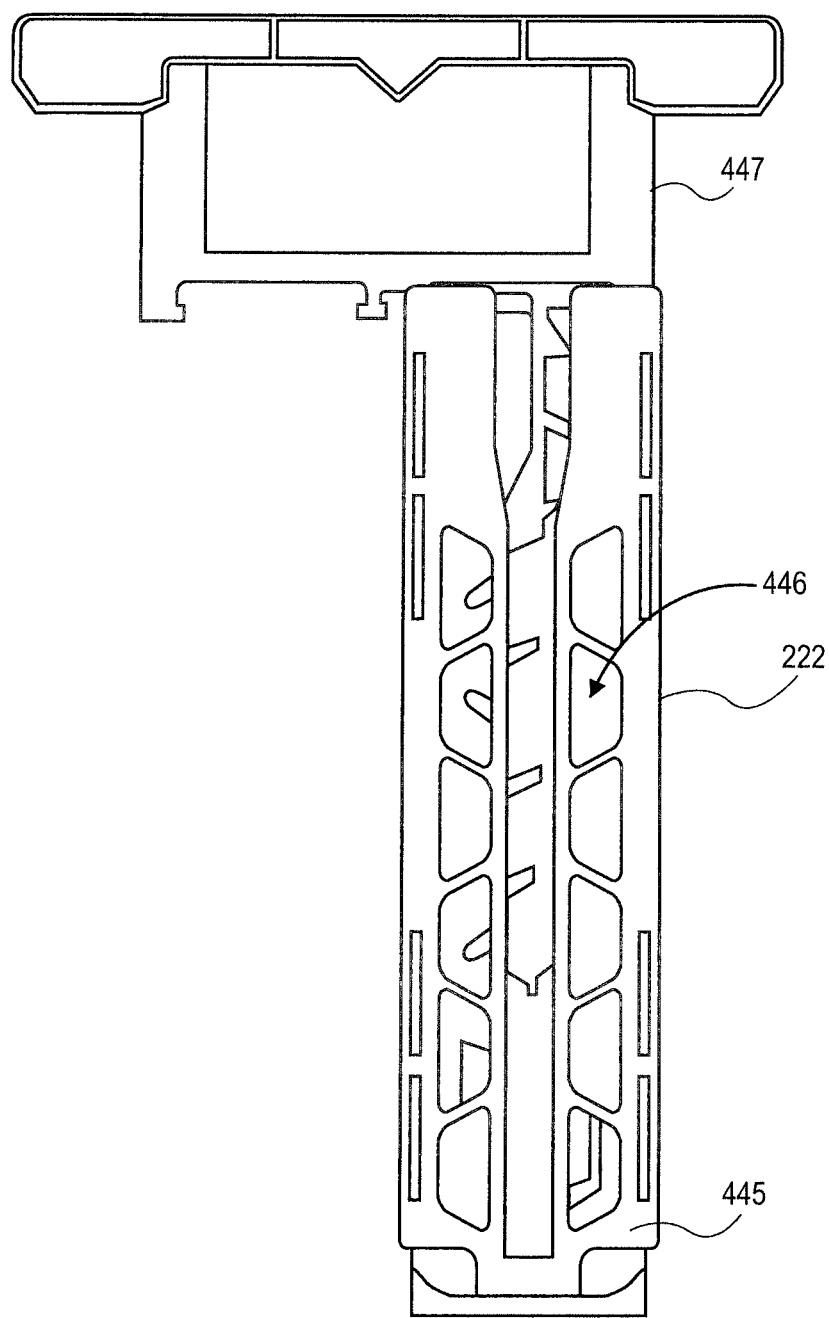
FIG. 4 is a representative embodiment of a magazine.

FIG. 4 is a representative embodiment of magazine 222 which is suitable. Magazine 222 includes door or cover 445 and compartment 446. Magazine 222 is held by hanger 447. In this embodiment, hanger 447 may support two magazines, though only magazine 222 is shown. A plurality of cassettes, such as, for example, about 20 cassettes, may be introduced into magazine 222, into predefined slots, divisions, or other cassette locations, with one cassette arranged vertically over another as viewed. Once the cassettes are loaded, door 445 may be closed, enclosing the cassettes in the magazine. As illustrated in FIG. 4, magazine 222 may have an open structure defining a generally large number of slits, holes, perforations, or other openings. An indication of compartment 446 is indicated by an arrow extending through an opening to point to the compartment. These openings may allow access to the cassettes by liquids, such as dehydrants, liquid wax, embedding agents, and the like. The magazine represents a convenient way to carry or handle multiple cassettes.

It is to be appreciated that the size, shape, design, appearance, materials, and manner of operation of cassettes and magazines may vary widely from one implementation to another. As such, the terms cassette and magazine are to be interpreted broadly as tissue holder or carrier devices, mechanisms, or structures. As used herein a cassette holds a single sample of tissue, whereas a magazine holds multiple samples of tissue, often with each tissue being held by a different corresponding cassette.

Referring again to FIG. 2, tissue processor 212 includes tissue processing mechanism 214. The tissue processing mechanism includes tissue drying mechanism 216 to dry or remove at least some of the fluid (e.g. water) from each of the tissues. Tissue drying mechanism 216 may include one or more dehydrants. Tissue drying mechanism 216 may also optionally include a clearing agent to clear the dehydrants from the tissue. Tissue drying mechanism 216 may also include a cassette handling mechanism to move the tissue around to the one or more dehydrants and/or clearants, and/or tubes or other flow conduits, and valves or other flow regulation devices, to move the one or more dehydrants and/or the clearants to the tissue.

Tissue processing mechanism 214 also includes infiltration mechanism 218 to infiltrate wax (e.g., paraffin), or another embedding agent (e.g., a polymer), into the tissue after a fluid removal operation. Infiltration mechanism 218 may include a source of liquid wax or another liquid embedding agent. In some cases, the infiltration mechanism may optionally include a vacuum to assist with the infiltration.

Magazine 222A having a plurality of cassettes, with each of the cassettes having a processed tissue, may be output from the tissue processor at output 220. Each processed tissue may represent a dried and infiltrated tissue, from which at least some of the fluid (e.g. water) has been removed, and into which wax or another embedding agent has been infiltrated.

One particular example of a suitable tissue processor is the TISSUE-TEK® XPRESS® X120 brand rapid tissue processor, which is commercially available from Sakura Finetek USA, Inc., of Torrance, Calif. The TISSUE-TEK® XPRESS® X120 brand rapid tissue processor has one loading station and two unloading stations. After a magazine having cassettes has been loaded into the loading station, the TISSUE-TEK® XPRESS® X120 brand rapid tissue processor may use microwave heating technology, dehydrants, an embedding agent, and vacuum assisted infiltration techniques to perform tissue processing. A finished magazine having cassettes having dried and infiltrated tissue may be output through one of the two unloading stations.

Referring again to FIG. 2, integrated system 210 also includes tissue processor/embedding system integration unit 224. For convenience, the tissue processor/embedding system integration unit may be referred to herein simply as an integration unit. The integration unit may automate, or at least partially automate, the transfer of magazines or other tissue holders between the tissue processor and the embedding system.

The integration unit includes robot 226. The term robot is to be interpreted broadly as a conveyance, transfer device, electro-mechanical transfer device or mechanism, or automatically controlled, reprogrammable, multipurpose manipulator programmable in three, four, or more axes. Robot 226 may take various forms or configurations, consistent with its intended purpose. For example, in various embodiments, robot 226 may be a Gantry or Cartesian coordinate type robot, a selective compliant assembly robot arm (SCARA) type robot, an articulated arm type robot, or a combination thereof (e.g., a SCARA type robot coupled in a Gantry type robot configuration), to name just a few examples.

In one or more embodiments, robot 226 may have a robotic arm or other mechanical limb. The arm or limb may include an interconnected set of two or more links and one or more powered joints. In one or more embodiments, the arm or limb may allow rotation or movement in at least four axes. As is known, the flexibility or freedom of movement of the arm increases with increasing number of axes. The arm or limb may support and move an end-of-arm tooling or other end effector that is connected at the end of the arm or limb.

The end effector may allow the robot to perform certain intended functions, such as, for example, engaging with an item (e.g., a magazine or other tissue holder), holding and moving the item, and disengaging from the item. In one or more embodiments, the end effector may include a gripper. The gripper may serve as a "hand" to grasp, clasp, hook, or otherwise engage with, hold and move, and disengage from an item. As one example, the gripper may include two opposed jaws, claws, or fingers coupled at a joint, or a pincer-like mechanism, which is able to open and close. Alternatively, a more sophisticated gripper having three or more fingers may optionally be used. Another suitable end effector is a hook, which may be used to hook a ring, loop, opening in a handle, or other hookable structure on an item.

The integration unit and the robot are functionally or operatively coupled or connected with the tissue processor and the embedding system. In one or more embodiments, the output of the tissue processor and the input of the embedding system are within the "work envelope" of the robot.

In one or more embodiments, the integration unit and the robot may be physically coupled or connected between the tissue processor and the embedding system. For example, the robot may comprise a Gantry or Cartesian coordinate type robot having a track, rail, other horizontal member, or other linear axis extending between the tissue processor and the embedding system. A carriage including an arm or limb of the robot and the end effector may move along a linear axis between the tissue processor and the embedding system. Such a robot will be discussed in further detail below in conjunction with FIGS. 10A-10B. In addition to the linear axis, the integration unit may also optionally include a frame, chassis, housing, or the like to physically couple the tissue processor with the embedding system.

Alternatively, there may be no permanent physical coupling or connection between the integration unit, the tissue processor, and the embedding system. For example, the robot may include an articulated arm type robot between, in front of, behind, or otherwise proximate the tissue processor and the embedding system, without permanent physical connection. By proximate it is meant that the output of the tissue processor and the input of the embedding system are within the "work envelope" of the robot.

The robot may be programmed with an application program, program routine, or other set of instructions. The program or set of instructions may specify one or more operations the robot is to autonomously or at least semi-autonomously perform. Representatively, the program or set of instructions may specify the movements (e.g., coordinates, distances, directions, etc.), end effector actions, timing or triggers, and like information associated with the operations.

Referring again to FIG. 2, in one or more embodiments, as shown by arrow 228, robot 226 may transfer magazine 222A (or another tissue holder) from output 220 of tissue processor 212 to input 238 of embedding system 230. Input 238 of embedding system 230 may receive magazine 222B. The "A" and "B" in 222A and 222B, respectively, are used merely to indicate the same magazine in different locations. In a sense, the robot may represent a pick and place robot to pick and place the magazine.

Robotically transferring magazines or other tissue holders between the tissue processor and the embedding system, as opposed to manually transferring the magazines, offers certain potential advantages. For one thing, it may free personnel from the necessity of having to performing these sometimes repetitive or tedious operations manually. Advantageously, this may allow the personnel to perform more value-added operations and/or other operations less amenable to automation. For another thing, the robot may be better suited for performing these operations faithfully and timely than the personnel, who may at times be distracted with other tasks, or forget or be unable to perform these operations faithfully or timely. Advantageously, this may allow improved productivity or throughput by reducing instrument downtime waiting for samples to be transferred manually.

Referring again to FIG. 2, the embedding system includes embedding mechanism 232. The embedding mechanism may include cassette handling mechanism 234 to handle cassettes. In one embodiment, the cassette handling mechanism may include robotics internal to the embedding system. The cassette handling mechanism may remove cassettes from the magazine, and provide them to dispensing mechanism 236. The dispensing mechanism may include a source of liquid wax (e.g. paraffin) or another embedding medium, and may dispense the embedding medium on the cassettes and cool the embedding medium in order to embed the tissue in a block or other mass of the embedding medium.

One particular example of a suitable embedding system is the TISSUE-TEK® AUTOTEC® brand automated embedding system, which is also commercially available from Sakura Finetek USA, Inc. The TISSUE-TEK® AUTOTEC® brand automated embedding system has a loading station or input, and four output doors. After a magazine having cassettes has been input, the TISSUE-TEK® AUTOTEC® brand automated embedding system has internal robotics to handle the cassettes within the instrument. The TISSUE-TEK® AUTOTEC® brand automated embedding system places the cassettes in molds, dispenses paraffin or other embedding medium into the molds, and cools the embedding medium to form blocks or other masses in which the tissue is embedded. The cassettes having the tissue embedded in the blocks are then moved to one of the four output doors.

Figure 5:
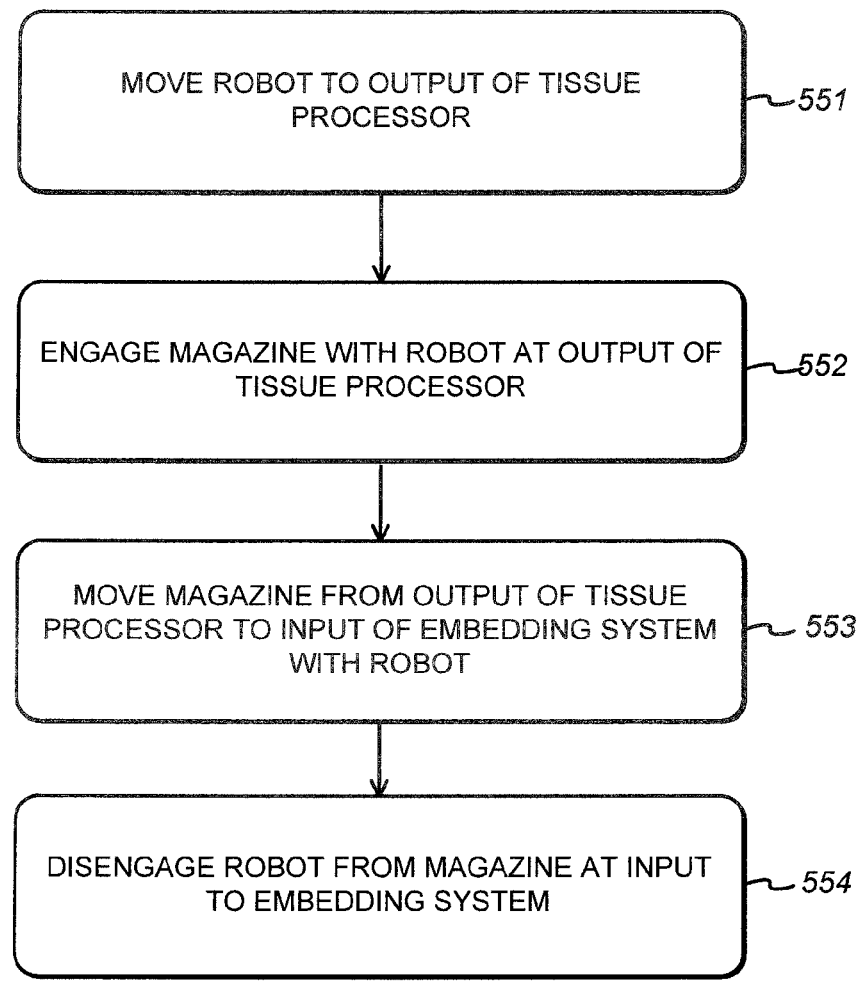
FIG. 5 is a block flow diagram of an embodiment of a method of robotically transferring a magazine from an output of a tissue processor to an input of an embedding system with a robot.

FIG. 5 is a block flow diagram of an embodiment of method 550 of robotically transferring a magazine or magazines (or other tissue holder) from an output of a tissue processor to an input of an embedding system with a robot. The magazines being transferred may have cassettes, and each of the cassettes may have a processed tissue, from which fluid has been at least partially or substantially removed, and into which wax or another embedding agent has been infiltrated.

The movement of a robot may be controlled by a controller (e.g., a programmable logic unit or a computer) that is electrically or communicatively linked to a tissue processor and an embedding system. In one or more embodiments, movement or operation of the robot may be based on signals exchanged between the controller and/or the integration unit and the tissue processor and/or the embedding system. For example, in one embodiment, such a controller may receive a signal from the tissue processor indicating that a magazine or magazines are in the tissue processor and are ready for embedding. In response, the controller may signal the robot to retrieve the magazine(s) from the tissue processor and transfer them to the embedding system.

At block 551, the robot may move to the output of the tissue processor. As used herein, moving the robot does not necessarily mean moving the whole robot. In one aspect, a portion of the robot (e.g., a portion having an end effector) may move, while another portion of the robot may remain stationary. Of course, the robot need not move if the robot already happens to be at the output of the tissue processor.

In one or more embodiments, prior to, at about the same time as, or shortly after the robot moves to the output, the tissue processor may autonomously open the output in order to provide the robot access to the magazine or a signal from the controller may result in the tissue processor opening the output. For example, the tissue processor may slide open a drawer, or open a door, cover, or other closure mechanism. In one or more embodiments, a conventional tissue processor may be modified to incorporate a small motor, actuator, other mechanism, or other means for opening the output. Alternatively, the robot may open the output, such as, for example, by pressing a button, flipping a switch, pulling on a drawer, opening a door, sliding open a cover, lifting a lid, or performing another action, such as, for example, an action that an operator would normally perform manually. Advantageously, this may allow a conventional tissue processor to be used without the aforementioned modification. Other approaches are also contemplated, for example, the controller may receive a signal indicating that a magazine is ready for transfer, and the robot may move to a position, in which movement to the position trips a switch or otherwise signals the output to open.

At block 552, the robot may engage with the magazine at the output of the tissue processor. For example, a gripper or other end effector may pinch, clamp, clasp, grip, grasp, or otherwise engage with the magazine. In some tissue processors, such as the TISSUE-TEK® XPRESS® X120 brand rapid tissue processor, instead of a single magazine being provided at the output, two or more magazines connected by a hanger or other connector may be provided at the output. The robot may potentially engage the hanger. As used herein, the robot engaging with the magazine, the robot engaging with the tissue holder, and like phrases, encompass the robot engaging with a hanger, other connector, or other structure connected to one or more magazines.

In one or more embodiments, when engaging the item, the robot may utilize native features or structures on the magazine or other tissue carrier to improve the engagement or holding on the item. For example, natural grooves, ridges, protrusions, handles, or the like may be utilized. As another option, in one or more embodiments, the magazine or other tissue carrier may be adapted or modified to include dedicated features or structures to improve the engagement or holding on the item. Examples of such features or structures include, but are not limited to, handles or other parts designed specifically to be engaged by the robot, loops, rings, or other hookable structures capable of being hooked by a hook, to name just a few examples.

At block 553, the robot may move the magazine from the output of the tissue processor to the input of the embedding system. As shown by arrow 228 in FIG. 2, in one or more embodiments, the robot may move the magazine from the output of the tissue processor directly to the input of the embedding system. Alternatively, as will be discussed further below, as shown by arrows 657 and 659 in FIG. 6, in one or more embodiments, the robot may move the magazine from the output of the tissue processor indirectly to the input of the embedding system via an intermediate storage location (e.g., storage location 656).

After the robot has moved the magazine out of the output of the tissue processor, in one or more embodiments, the tissue processor may autonomously close the output, or a controller may direct the tissue processor to close the output by sending an appropriate signal to the tissue processor. Alternatively, the robot may optionally close the output before moving away.

In one or more embodiments, prior to, at about the same time as, or shortly after the robot moves to the input of the embedding system, the embedding system may autonomously open the input, or be directed to open the input by a controller. For example, the embedding system may slide open a drawer, or open a door, cover, lid, or other closure mechanism. In one or more embodiments, an otherwise conventional embedding system may be modified to incorporate a small motor, actuator, other mechanism, or other means for opening the input. By way of example, the TISSUE-TEK® AUTOTEC® brand automated embedding system may be modified so that lead screws may be rotated to move a drawer outward. Alternatively, the robot may open the input, such as, for example, by pressing a button, flipping a switch, pulling on a drawer, sliding open a cover, lifting a lid, or performing another action, such as an action that an operator would normally perform manually. This may allow a conventional embedding system to be used without modification.

Some embedding systems may have two or more drawers or other locations where tissue holders may be input. In one or more embodiments, the embedding system may provide a signal or communication to the robot indicating one of the locations where the tissue holder is to be input. The robot may then move the tissue holder to the indicated location.

At block 554, the robot may disengage from the magazine at the input to the embedding system. For example, the magazine may be dropped or otherwise loaded into the input of the embedding system. Then, the input to the embedding system may be closed, either autonomously by the embedding system, or by the robot. At this point, embedding may be performed in a conventional manner.

Figure 6:
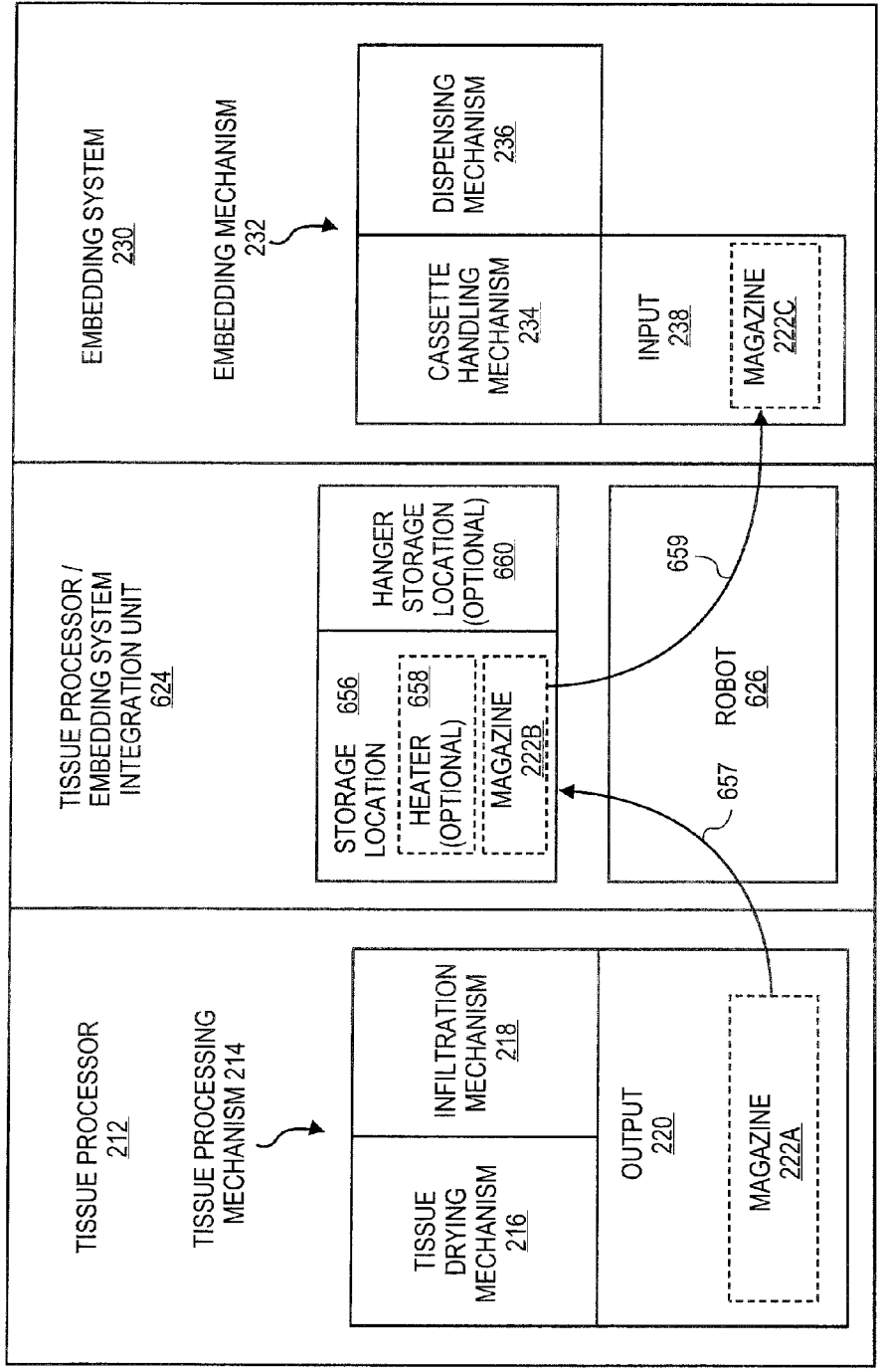
FIG. 6 is a block diagram of a second embodiment of an integrated tissue processing and embedding system.

FIG. 6 is a block diagram of a second embodiment of integrated tissue processing and embedding system 610, which for convenience may simply be referred to as integrated system. The integrated system includes tissue processor 212 and embedding system 230. The tissue processor and the embedding system, and their components and functions, may optionally be similar to, or the same as, those of FIG. 2. To avoid obscuring the description, these aspects will not be repeated.

The integrated system also includes tissue processor/embedding system integration unit 624, or simply the integration unit. In an embodiment where a controller is linked to a tissue processor and an embedding system to control the transfer of a magazine(s) from the tissue processor to the embedding system, the controller may also be electronically linked to the integration unit.

Integration unit 624 has robot 626. Robot 626, and its components and functions, may be similar to those of robot 226 of FIG. 2, with a few notable exceptions discussed below.

As shown, in one or more embodiments, the integration unit may include storage location 656. The storage location may be used to store magazines or other tissue holders. The storage location is located outside of the tissue processor and the embedding system. Representatively, in various embodiments, the storage location may include a drawer, chamber, compartment, cabinet, enclosure, cubbyhole, or the like. The robot may be capable of introducing the magazine into the storage location, and removing the magazine from the storage location.

In one or more embodiments, as shown by arrow 657, robot 626 may transfer magazine 222A from output 220 of tissue processor 212 to storage location 656. Subsequently, in one or more embodiments, as shown by arrow 659, the robot may transfer magazine 222B from the storage location to input 238 of embedding system 230 as magazine 222C.

As shown, in one or more embodiments, the integration unit may optionally include heater 658 to heat the storage location and/or the magazine or at least the tissue located in the storage location. The heater may be within the storage location or proximate the storage location. Examples of suitable heaters include, but are not limited to, heat lamps (e.g., light bulbs that give off heat), heating coils, heating elements, resistance heaters, hot plates, hot pads, pipes having hot water or other heating fluid flowing through them, electric heaters, radiative heaters, space heaters, and the like. In one or more embodiments, the heater may heat the storage location to a temperature in a range of about 50° C. to about 80° C., or from about 55° C. to about 75° C., or from about 58° C. to about 72° C. If desired, the integration unit may optionally include a temperature control system (not shown) to control the heater to attempt to maintain or control a temperature within the storage location and/or a temperature proximate the tissue.

As shown, in one or more embodiments, the integration unit may optionally include hanger storage location 660 to store a hanger or other connector that is used to connect two or more magazines. As previously discussed, some tissue processors, such as, for example, the TISSUE-TEK® XPRESS® X120 brand rapid tissue processor, provide two or more magazines connected by a hanger or other connector. The robot may be capable of disconnecting or otherwise removing the hanger or other connector from the magazines, and introducing the hanger or other connector into the hanger storage location. Examples of suitable hanger storage locations include, but are not limited to, a rack, a rod, a ring, a hook, or another structure or device that a hanger may be hung on. Alternatively, the robot may instead move the hanger to another location, such as back to the tissue processor.

Figure 7:
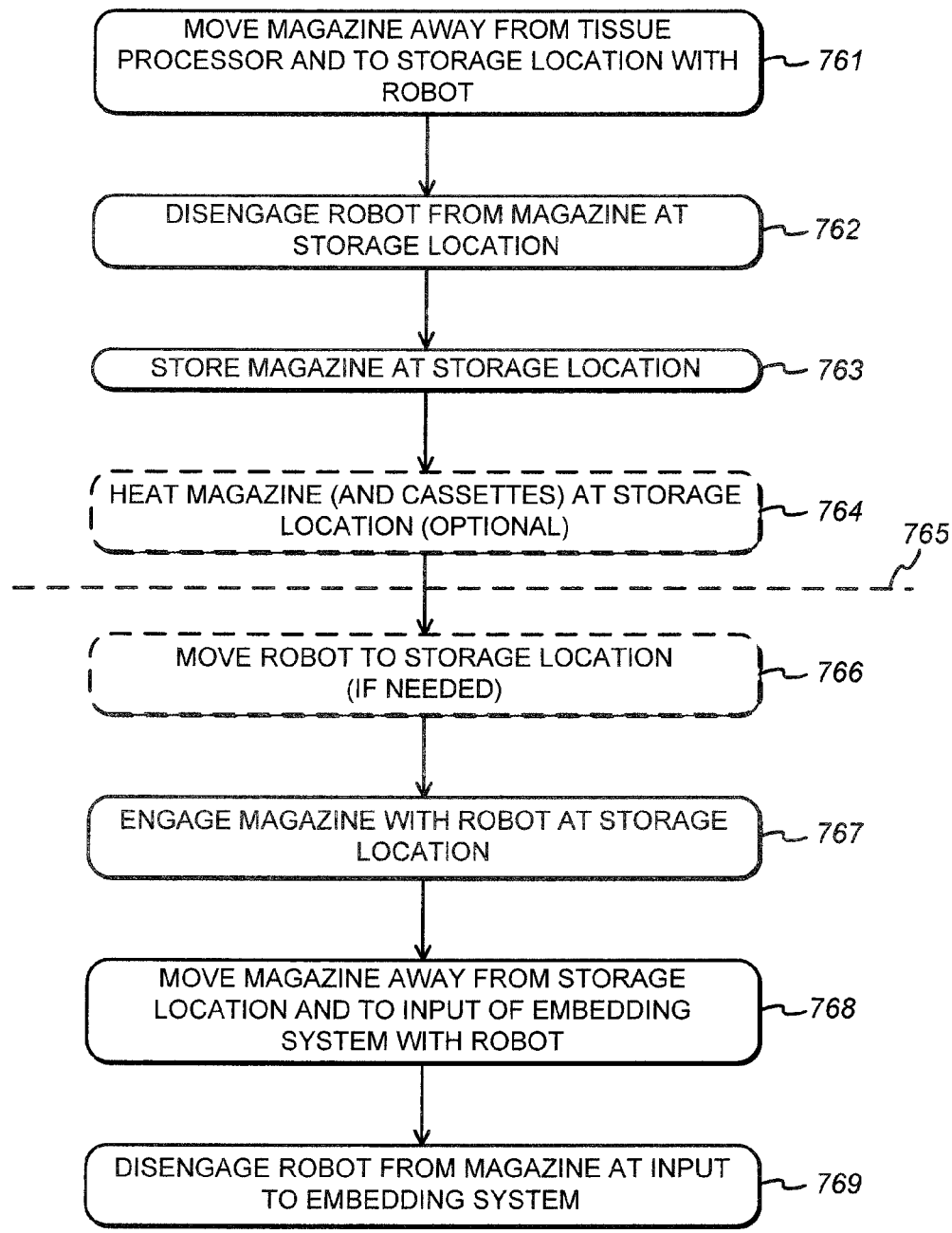
FIG. 7 is a block flow diagram of an embodiment of a method of robotically transferring a magazine from an output of a tissue processor indirectly to an input of an embedding system via an intermediate storage location.

FIG. 7 is a block flow diagram of an embodiment of a method 753 of robotically transferring or moving a magazine (or other tissue holder) from an output of a tissue processor indirectly to an input of an embedding system through an intermediate storage location with a robot.

At block 761, the robot may move the magazine away from the tissue processor and to the storage location, such as, for example, storage location 656 of integration unit 624. In one or more embodiments, prior to, at about the same time as, or shortly after the robot moves to storage location, the integration unit and/or the robot may potentially autonomously open the storage location. For example, the integration unit may slide open a drawer, or open a door, cover, lid, or other closure mechanism. Alternatively, the robot may open the storage location, such as, for example, by pressing a button, flipping a switch, pulling on a drawer, sliding open a cover, lifting a lid, or the like.

At block 762, the robot may disengage from the magazine at the storage location. If the magazine is connected to a hanger or other connector, along with potentially one or more other magazines, then the robot may decouple the hanger or other connector from the magazine(s). The robot may move the hanger or connector to a hanger storage location, such as, for example, hanger storage location 660.

In one or more embodiments, after the robot disengages from the magazine and moves out of the storage location, the integration unit and/or the robot may potentially close the storage location. Note that it is not required that the storage location be capable of being opened and closed.

At block 763, the magazine may be stored at the storage location. In one or more embodiments, on average the magazine may be stored at the storage location for at least a brief period of time ranging from about at least one minute to about an hour, often from about two minutes to about twenty minutes. Occasionally, such as, for example, if the embedding system needs additional cassettes, the time may be shorter, or occasionally, such as, for example, if the embedding system is down, has plenty of cassettes, or the like, the storage period may be longer.

At block 764, the magazine, or at least the infiltrated tissue, may optionally be heated while at the storage location. For example, heater 658 may heat the storage location, the magazine, the cassettes, and/or the infiltrated tissue. In one or more embodiments, the infiltrated tissue may be exposed to a temperature operable to heat the wax or other embedding agent in the tissue to a softening or melting point over a period ranging from about 2 to about 20 minutes, in some cases from about 5 to 15 minutes. Temperatures conventionally employed in the input of the TISSUE-TEK® AUTOTEC® brand automated embedding system are suitable. However, this particular heating is not required, since any heating may offer an advantage.

Conventionally, some embedding systems, such as, for example, the TISSUE-TEK® AUTOTEC® brand automated embedding system, heat the infiltrated tissue for a period of time in the input before beginning the embedding process. The time taken to heat the infiltrated tissue in the input tends to increase the processing time for embedding and/or limit the throughput of the embedding system. One advantage of heating the infiltrated tissue in the storage location is a reduction of the time needed to heat the tissue in the input of the embedding system. This can help to reduce the processing time for embedding and/or improve the throughput of the embedding system. Furthermore, some embedding systems may potentially lack the ability to pre-heat the tissue before the actual embedding.

Referring to FIG. 7, dashed line 765 is used to indicate a second half of method 753, in which the magazine is transferred or moved from the storage location to the input of the embedding system. Different criteria are possible for determining when to begin the second half of the method.

In one or more embodiments, the second half of the method may begin when the embedding system is ready to receive and/or process the magazine or tissue. For example, the embedding system may be capable of signaling to the integration unit that the embedding system is or will be ready to receive and/or process the magazine or tissue. This may be done through a control system (e.g., a programmable logic unit, a computer system, or other controller) that queries the embedding system whether it is ready to accept magazines for embedding (e.g., a load dock is queried whether it is empty and the embedding system is queried whether a new process can begin). Alternatively, in one or more embodiments, the second half of the method may begin when the magazine has been stored at the storage location for a predetermined or fixed period of time.

At block 766, the robot may move to the storage location. Of course, the robot need not move if the robot already happens to be at the storage location.

In one or more embodiments, prior to, at about the same time as, or shortly after the robot moves to the storage location, the integration unit and/or the robot may autonomously open the storage location (e.g., a controller may signal the integration unit to open the storage location).

At block 767, the robot may engage with the magazine at the storage location. At block 768, the robot may move the magazine away from the storage location and to the input to the embedding system.

In one or more embodiments, prior to, at about the same time as, or shortly after the robot moves to the input of the embedding system, the embedding system may autonomously open the input of the embedding system. Alternatively, the robot may open the input of the embedding system.

At block 769, the robot may place the magazine in the embedding system at the input and disengage from the magazine at the input to the embedding system. In one or more embodiments, after the robot disengages from the magazine and moves from the input, the embedding system may autonomously close the input of the embedding system (e.g., a controller may signal the embedding system to close the input). Alternatively, the robot may close the input.

At this point, embedding may be performed in a conventional manner. At some point, the embedding system will have removed all of the cassettes from the magazine. Accordingly, an empty magazine may exist at the embedding system. In one or more embodiments, an integration unit and/or a robot may optionally be capable of removing empty magazines from the embedding system. Advantageously, this may avoid the need to manually remove the empty magazine.

Figure 8:
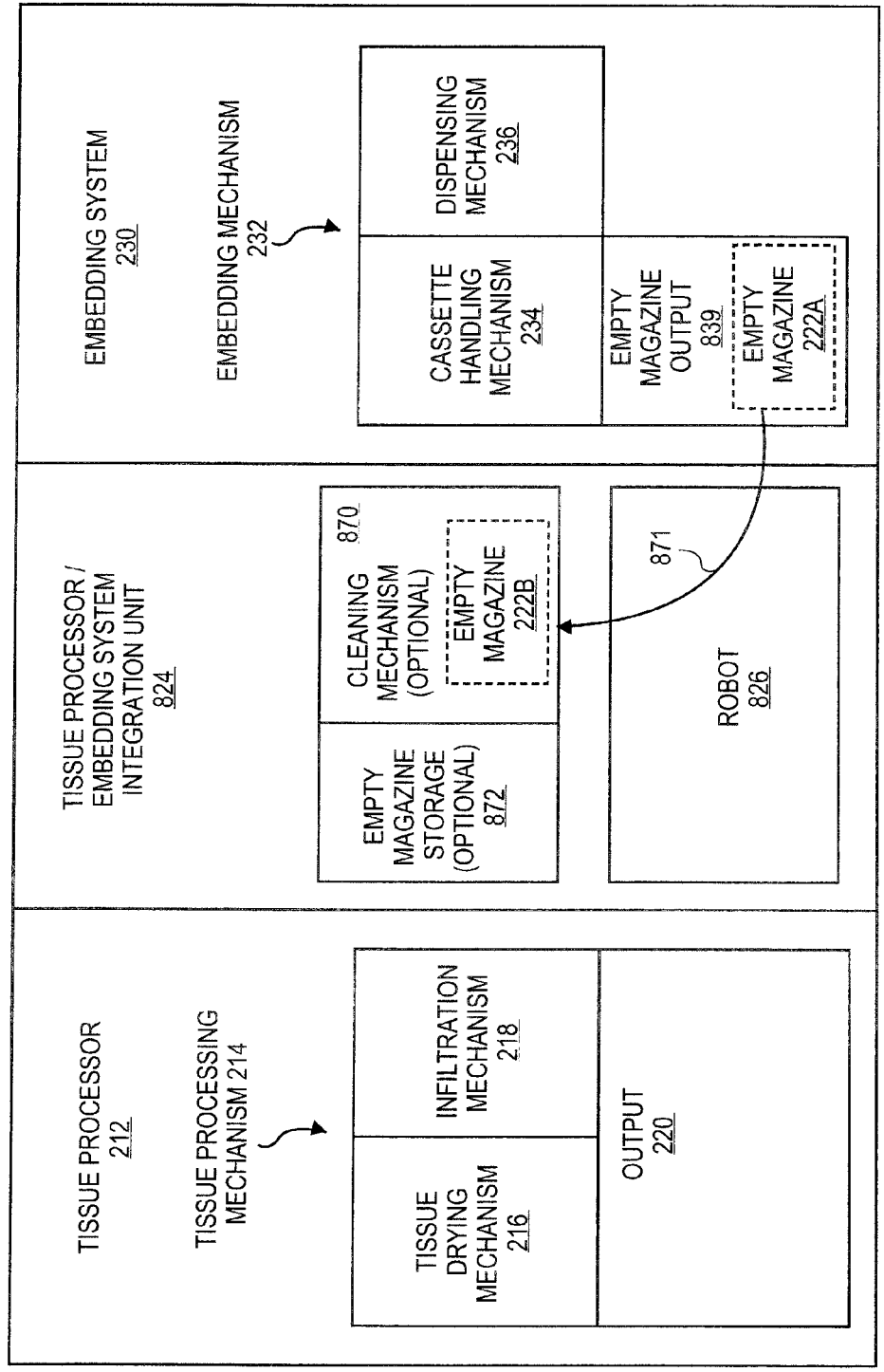
FIG. 8 is a block diagram of another embodiment of an integrated tissue processing and embedding system.

FIG. 8 is a block diagram of another embodiment of integrated tissue processing and embedding system 810, which for convenience may simply be referred to as an integrated system. The integrated system includes tissue processor 212 and embedding system 230. The tissue processor and the embedding system, and their components and functions, may optionally be similar to, or the same as, those of FIG. 2 and/or FIG. 6. To avoid obscuring the description, these aspects will not be repeated.

The integrated system also includes tissue processor/embedding system integration unit 824, which may simply be referred to as an integration unit. The integration unit has robot 826. Robot 826 and its components and functions may be similar those of robot 226 of FIG. 2 and/or robot 626 of FIG. 6, with a few notable exceptions discussed below.

As shown, in one or more embodiments, the integration unit may optionally include cleaning mechanism 870 housed within the integration unit as a subsystem to clean empty magazines. In one or more embodiments, cleaning the empty magazines may include removing wax from the empty magazines. Examples of suitable cleaning mechanisms include, but are not limited to, hot water power washing (e.g., a flow of at least slightly pressurized heated water, for example heated to a temperature in a range of about 70° C. to about 95° C., or from about 77° C. to about 87° C., with or without soap (often without soap so that the water can more easily be recycled), directed at the empty magazines), baths of dewaxing solvents or compositions, showers of dewaxing solvents or compositions, a hot water bath, a hot water shower, a steam treatment, heating to above the melting point of wax, a scrubbing mechanism, or the like, or combinations thereof. By way of example, the cleaning mechanism may be provided in a drawer, chamber, compartment, cabinet, enclosure, vessel, or the like. The robot may be capable of introducing the empty magazines into the cleaning mechanism.

In one or more embodiments, as shown by arrow 871, robot 826 may transfer empty magazine 222A from empty magazine output 839 of embedding system 230 to cleaning mechanism 870 as empty magazine 222B.

As shown, in one or more embodiments, the integration unit may optionally include empty magazine storage 872 to store empty magazines, which may potentially have been cleaned by cleaning mechanism. Examples of suitable empty magazine storage include, but are not limited to compartments, enclosures, drawers, cabinets, cubbyholes, shelves, hangers, racks, hooks, sacks, and the like.

Figure 9A:
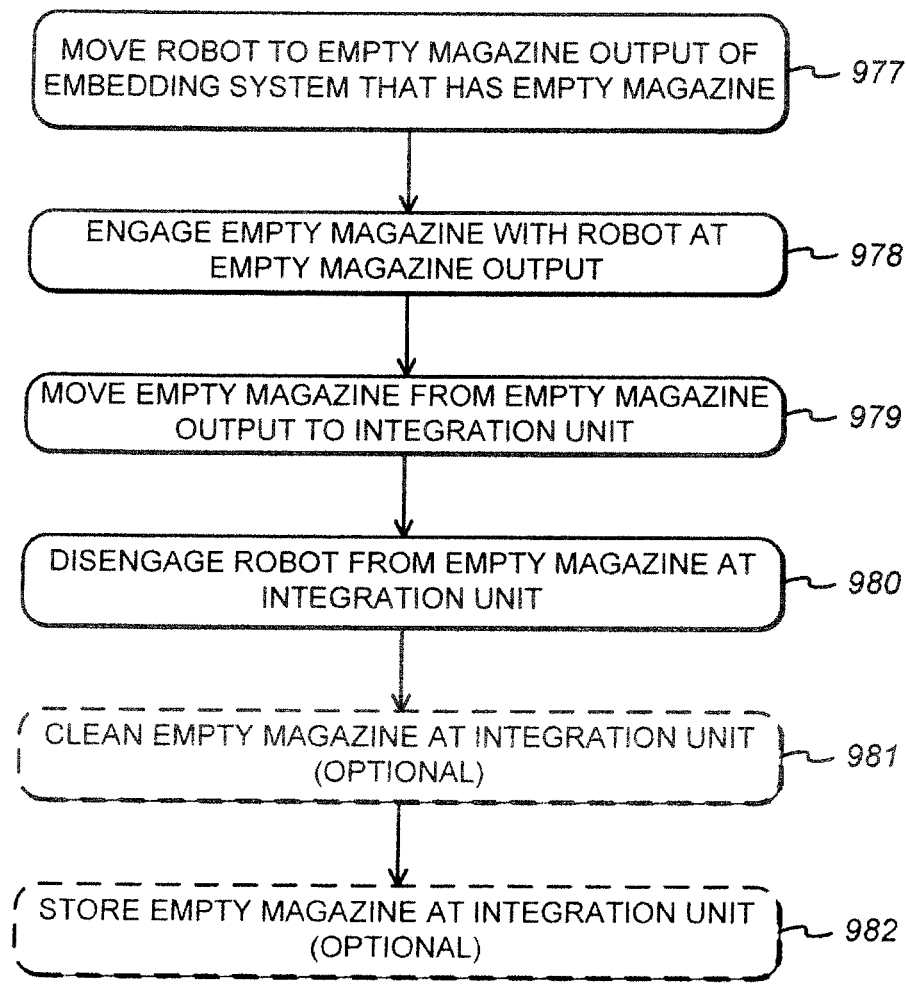
FIG. 9A is a block flow diagram of an embodiment of a method of robotically transferring an empty magazine from an empty magazine output of an embedding system to an integration unit.

FIG. 9A is a block flow diagram of an embodiment of a method 976 of robotically transferring or moving an empty magazine from an empty magazine output of an embedding system to an integration unit.

In one or more embodiments, the embedding system may signal or communicate to the integration unit, control logic for the robot, and/or the robot that the empty magazine is available (e.g., the last cassette has been removed from the magazine). In one or more embodiments, the signal or communication may also indicate one of multiple drawers or other locations where the empty magazine is located. Alternatively, in one or more embodiments, the integration unit and/or the robot may include software or other logic to calculate or estimate when the empty magazine will be available (e.g., based on when the full magazine was delivered and historical or otherwise known embedding system processing rates).

At block 977, the robot may move to the empty magazine output of the embedding system. Just prior to, at about the same time as, or shortly after the robot moves to the empty magazine output, in one or more embodiments, the embedding system may autonomously open the empty magazine output. Alternatively, the robot may open the empty magazine output.

At block 978, the robot may engage the empty magazine at the empty magazine output. At block 979, the robot may lift the empty magazine out of the output and move the empty magazine from the empty magazine output to the integration unit.

After the empty magazine has been removed from the output, in one or more embodiments, the embedding system may autonomously close the empty magazine output. Alternatively, the robot may close the empty magazine output.

At block 980, the robot may disengage from the empty magazine at the integration unit. In various embodiments, the robot may disengage from the empty magazine at a cleaning mechanism (e.g., cleaning mechanism 870) of the integration unit or at an empty magazine storage (e.g., empty magazine storage 872) of the integration unit.

At block 981, the empty magazine may optionally be cleaned at the integration unit. In one or more embodiments, cleaning the magazine may include removing wax from the empty magazine. Advantageously, this may avoid the need for personnel to manually clean the empty magazines.

At block 982, the empty magazine, which has potentially been cleaned, may optionally be stored at the integration unit, such as at empty magazine storage 872. The robot may be capable of moving the empty magazines from the cleaning mechanism to the empty magazine storage. Alternatively, the empty magazine may optionally be stored elsewhere, such as, for example, at the tissue processor, the embedding system, or other locations within the working envelope of the robot (e.g., on a table or work surface proximate the robot).

FIGS. 7 and 9 show example methods. These methods have been described in a basic form, but operations may optionally be added to and/or removed from the methods. Furthermore, certain operations of the methods may also optionally be performed in different order. For example, the second half of method 753 of FIG. 7 (shown below dashed line 765) may optionally be performed after at least part of method 976 of FIG. 9A has been performed. The order of such operations may be readily changed by changing the application program or set of instructions used to control the operations performed by the robot.

Figure 9B:
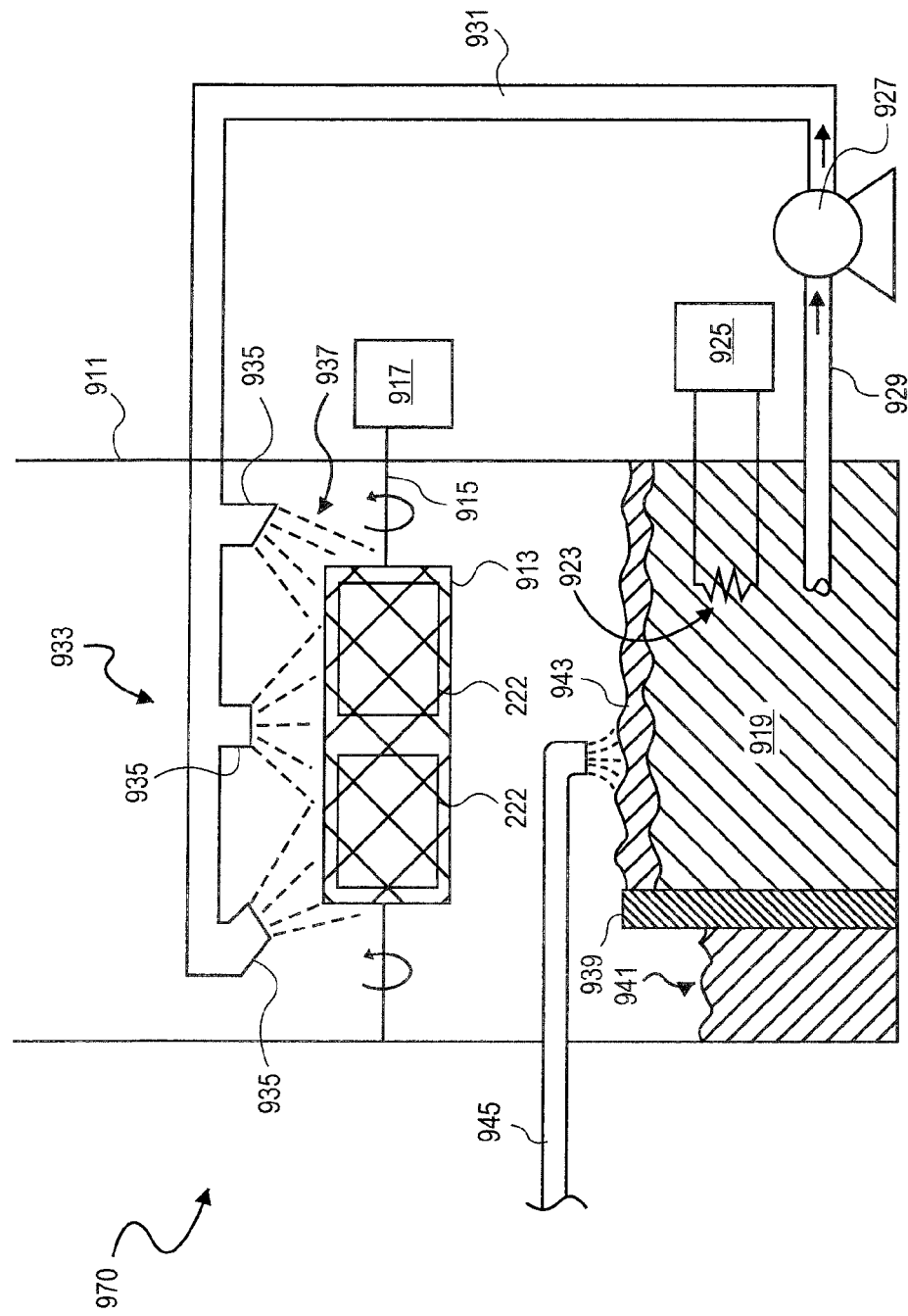
FIG. 9B illustrates an embodiment of a cleaning mechanism.

FIG. 9B illustrates an embodiment of a cleaning mechanism 970. In one or more embodiments, the cleaning mechanism may be included in an integration unit.

The cleaning mechanism includes a tank 911. Inside the tank is a mesh or other openwork basket 913. During operation, one or more or a plurality of empty magazines 222, potentially having wax thereon, may be introduced into and closed within the basket.

As shown, the basket may optionally be coupled with a rotation mechanism that may include a spindle, shaft, or other rotation axis 915 that rotates to rotate the basket and a motor or other rotation actuator 917 to rotate the rotation axis. In the illustration, the basket rotates along a horizontal axis, although the basket may alternatively rotate along a vertical axis. The basket may also optionally move horizontally or vertically along the horizontal or vertical axis, if desired, for example to help to improve cleaning, although this is not required.

A bottom portion of the tank may serve as a sump or reservoir. Water 919 may be included in the sump or reservoir.

A heater 923 may be disposed in the water and used to increase the temperature of the water. In one or more embodiments, the temperature of the water may be increased to a temperature ranging from about 70° C. to about 100° C., often from about 75° C. to about 95° C., in some cases from about 82° C. to about 87° C. Examples of suitable heaters include, but are not limited to, immersion heaters including an electric resistance heater, boilers of the type used in home hot water heaters, steam coils, and the like. If desired, a heater or temperature controller 925 may optionally be included to control the heater and/or to control the temperature.

A pump 927 or other water movement and/or pressurization device may draw water from the sump or reservoir through an inlet line 929. The pump may pressurize the water. For example, in one or more embodiments, the pump may pressurize the water to a pressure ranging from several hundred PSI (pounds per square inch) to several thousand PSI, and in some cases from about 500 PSI to about 1500 PSI. The output of the pump is coupled with a pressurized water line 931 capable of handling the output pressure.

A pressurized water ejection manifold 933 is coupled with the pressurized water line. The manifold may include one or more water jets or nozzles 935. Three jets or nozzles are shown in the illustrated embodiment, although fewer or more may optionally be included. The jets or nozzles are generally arranged around the basket so that sprays 937 therefrom are directed at substantially all portions of the empty magazines, at least when the basket is rotated.

The heated water may help to melt wax on the empty magazines. The pressurized sprays of the water may help to dislodge or remove the melted wax from the empty magazines. The removed wax may fall to the reservoir or sump at the bottom of the tank. There the wax, being lighter than the water, may tend to float as a melted and immiscible layer 943 on the water. As shown in one or more embodiments, an opening or inlet to inlet line 929 may be disposed within the water in sump or other bottom portion of the tank well below melted wax layer 943. This may help to avoid or at least reduce the drawing of melted wax into inlet line 929 by the pump.

In one or more embodiments, a ledge, weir, overflow dam, or other structure 939 may optionally be included projecting from the bottom of the tank upward to an intended level of fluid in the tank. Melted wax may flow over the ledge, weir, or other structure into a wax removal reservoir 941. Alternatively, the wax may be removed by other means, such as, for example, through a siphon port, from the top of the tank, or otherwise.

A water makeup line 945, such as, for example, connected with a faucet or other water supply, may optionally be used to add additional water to the tank. If desired, a level control system and a valve on the water makeup line (not shown) may optionally be included to control the level of the water in the tank. Collecting the water in the bottom of the tank may allow the water to be reused.

Figure 10A:
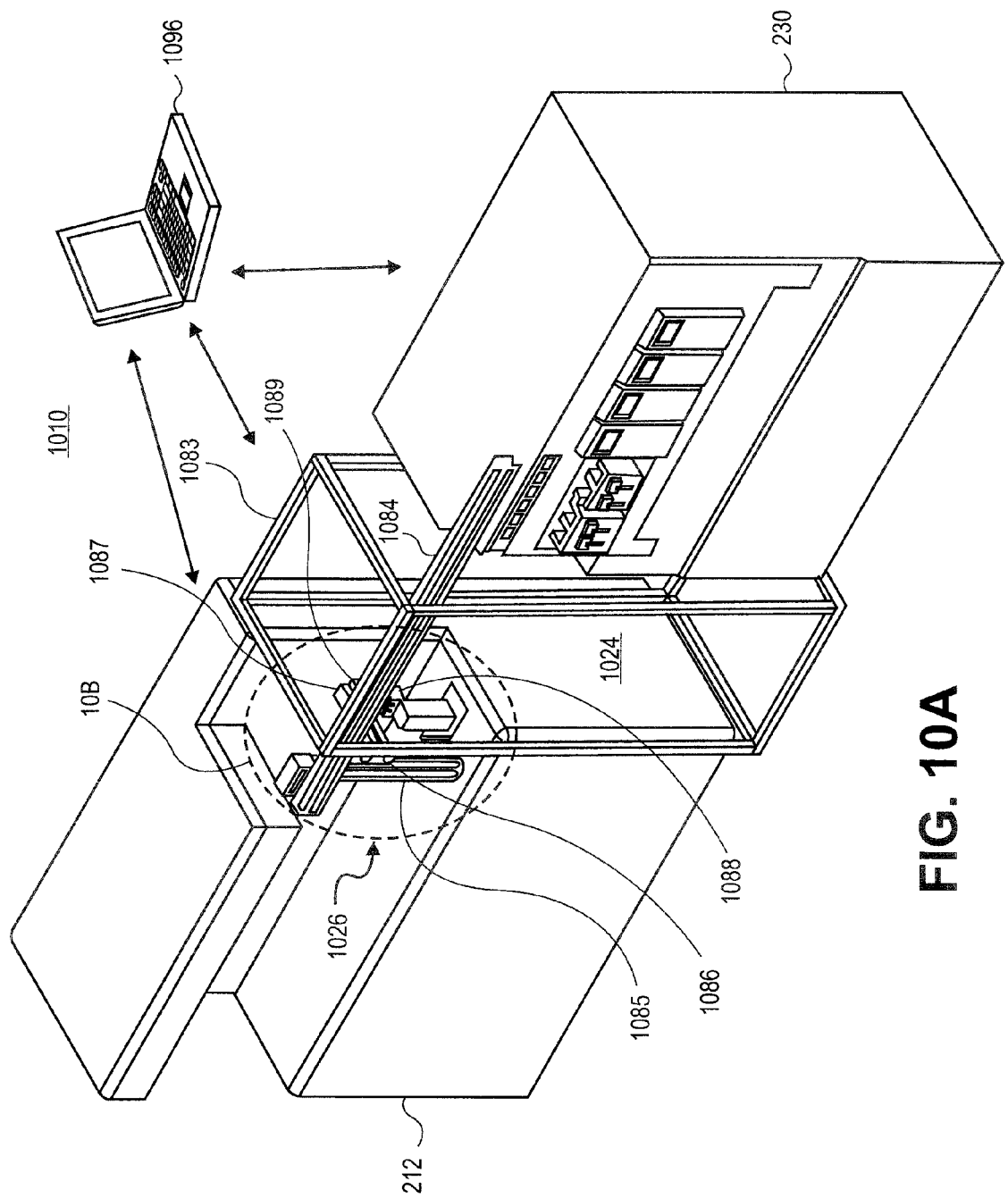
FIG. 10A is a diagram of another embodiment of an integrated tissue processing and embedding system.

FIG. 10A is a diagram of another detailed example embodiment of an integrated tissue processing and embedding system 1010, which for convenience may simply be referred to as an integrated system. The integrated system includes tissue processor 212 and embedding system 230. The tissue processor and the embedding system, and their components and functions, may optionally be similar to, or the same as, those of FIG. 2 and/or FIG. 6 and/or FIG. 8.

The integrated system also includes tissue processor/embedding system integration unit 1024, or simply the integration unit. The integration unit has robot 1026. Robot 1026 and its components and functions may be similar those of robot 226 of FIG. 2 and/or robot 626 of FIG. 6 and/or robot 826 of FIG. 8, with a few notable exceptions discussed below.

As shown, in one or more embodiments, the robot may have a so-called Cartesian Coordinate type or a gantry type arrangement. The integration unit includes frame 1083 to provide a structural support for the integration unit. The frame may be physically coupled or connected between the tissue processor and the embedding system, or just physically disposed between the tissue processor and the embedding system without physical contact. As shown, frame 1083 may have an open rectangular structure with beams, braces, or other members connecting the corners. Other frames having other sizes, shapes, and designs are also suitable.

Other components of the integration unit, such as, for example, a storage location, a heater, a cleaning mechanism, an empty magazine storage, and a hanger storage location, a controller, which for the sake of simplicity are not shown, may be housed within and coupled with the frame. For example, commercially available compartments, chambers, tanks, cabinets, or the like, may be introduced into and coupled with the frame, or, the compartments, cabinets, or the like, may be constructed onto the frame.

The robot is supported by frame 1083. As viewed, robot 1026 includes horizontal rail, track, beam, or other member 1084. The horizontal member is physically coupled or connected with and supported by the frame. The horizontal member is fixedly or statically coupled or connected in place and for purposes of this discussion its horizontal orientation defines an x-direction.

The horizontal member runs horizontally in a direction of an x-axis, which leads from the tissue processor to the embedding system. The horizontal member extends horizontally approximately from above the output of the tissue processor to above the input of the embedding system.

The robot also includes vertical rail, track, beam, or other member 1085. An uppermost portion of the vertical member is coupled or connected with the horizontal member at an intersection or "T". The vertical track or other member is slideably coupled with the horizontal member and the vertical member may slide horizontally along the horizontal member. For purposes of this discussion, the vertical orientation of vertical member 1085 defines a z-direction.

The vertical member runs vertically in a direction of a z-axis, which leads downward from horizontal member 1084. Vertical member 1085 extends vertically from horizontal member 1084 down approximately to the lower of either the output of tissue processor 212 or the input of embedding system 230. In the illustration vertical member 1085 leads downward toward the output of tissue processor 212. Vertical member 1085 is typically shorter in length than horizontal member 1084.

The robot also includes carriage 1086. Carriage 1086 is slideably or otherwise moveably mounted on, or otherwise moveably coupled or connected with, the horizontal and/or vertical members. Representatively, the carriage may be driven or moved by a motorized mechanism of the type used in Gantry robots. Electrical power may be provided to the carriage and/or the motor, for example, through a power supply train or chain along rails defining horizontal member 1084 and vertical member 1085.

Carriage 1086 may move along horizontal member 1084 and vertical member 1085. Horizontal member 1084 represents a horizontal linear x-axis of movement for the carriage. The vertical member represents a vertical linear z-axis of movement for the carriage. A path of movement of carriage 1086 of the robot along horizontal member 1084 is continuously connected with a path of movement of carriage 1086 of the robot along vertical member 1085. Vertical member 1085 may slide along horizontal member 1084 and carriage 1086 may slide or travel vertically along vertical member 1085. Together, the horizontal and vertical members define a continuous path for movement of the carriage from near the output of tissue processor 212 to near the input to embedding system 230.

One advantage of this vertical member 1085 is that it allows the robot access to inputs and outputs having, potentially, different elevations. However, vertical member 1085 is included in the illustrated embodiment to allow the carriage of the robot to reach the output of tissue processor 212 and/or the input of embedding system 230. If instead the output of tissue processor 212 and the input of embedding system 230 were higher, vertical member 1085 may potentially be omitted.

The robot also has arm 1087 and end effector 1088. Arm 1087 is connected with carriage 1086. End effector 1088 is connected with an end of arm 1087. Many known robot arm designs are suitable.

In one or more embodiments, arm 1087 may have rotation joint or other rotation mechanism 1089. Rotation mechanism 1089 is connected between an end of arm 1087 of the robot and end effector 1088. The rotation joint or mechanism may allow rotation of the end effector, in some cases in 360°. The rotation joint or mechanism combined with the horizontal and vertical members may give the robot at least four-axes of movement. By way of example, once the carriage is in an appropriate position, the robot may rotate the end effector to achieve a desired orientation to engage with an item, and/or to achieve a desired orientation to place the item in a location.

Typical Gantry type robots generally have less than four-axes of movement. For example, a typical Gantry type robot may have only three-axes of movement. Moreover, typical Gantry type robots generally do not have such a rotation mechanism 1089 that allows end effector 1088 to rotate. Still further, a typical Gantry type robot generally does not have the vertical track or other vertical member, such as vertical member 1085.

The integration unit also includes controller 1096 electrically, wirelessly, or otherwise linked or in communication with the robot. As shown, in one or more embodiments, the controller may include a computer system. Alternatively, the controller may include a programmable logic unit. The controller may include software or other instructions to control the robot. The controller may be programmable and optionally re-programmable. The controller may signal or communicate with the robot to cause the robot to perform operations as described elsewhere herein.

As shown, in one or more embodiments, controller 1096 may also optionally be electrically, wirelessly, or otherwise linked or in communication with the tissue processor and/or the embedding system. In one or more embodiments, the controller may receive signals or communications from the tissue processor and/or the embedding system, such as, for example indicating status (e.g., a processed magazine is ready, the embedding system is ready, an empty magazine is ready in the embedding system, etc.). In one or more embodiments, the controller may provide signals or communications to the embedding system and/or the tissue processor to control the embedding system and/or the tissue processor to open and/or close their respective inputs and outputs.

In one or more embodiments, the controller may also optionally control other aspects associated with the operation of the integration unit. For example, in one or more embodiments, the controller may control heating of a storage location (e.g., temperatures, start times, stop times, durations, or some combination thereof). As another example, in one or more embodiments, the controller may control a cleaning mechanism (e.g., start times, stop times, temperatures, pressures, or some combination thereof).

Figure 10B:
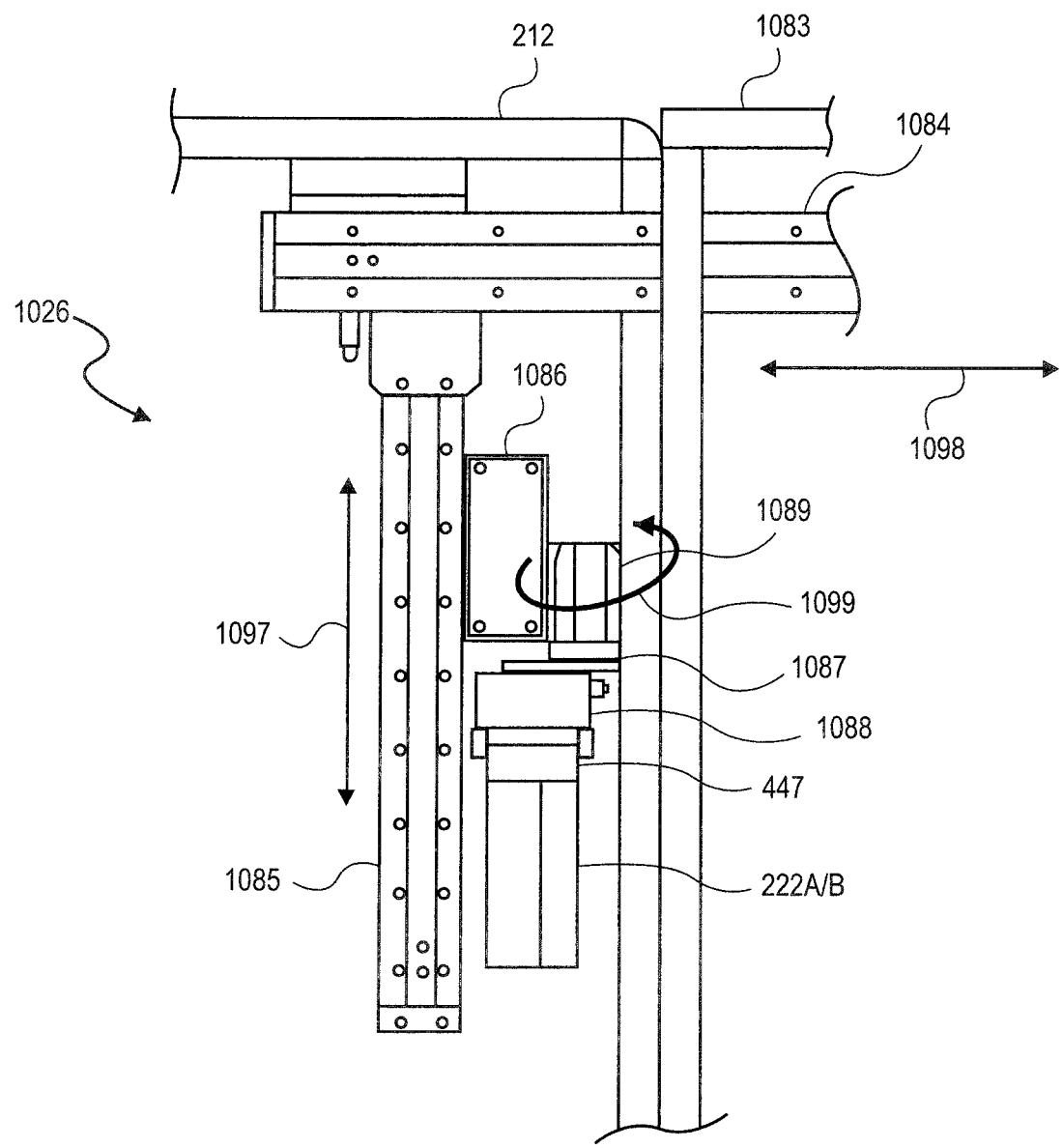
FIG. 10B is an expanded front view of the robot of FIG. 10A.

FIG. 10B is an expanded front view of robot 1026 of FIG. 10A. A portion of tissue processor 212 and frame 1083 are shown.

Robot 1026 includes horizontal member 1084 (only a portion of which is shown) coupled with vertical member 1085. The robot also includes carriage 1086. In the illustration, the carriage is coupled with the vertical member. The carriage may slide or otherwise move vertically along the vertical member in the direction of vertical arrow 1097. The carriage may slide or otherwise move horizontally along the horizontal member in the direction of horizontal arrow 1098.

The robot also has arm 1087 and end effector 1088. The arm is coupled or connected with the carriage. The end effector is coupled or connected with the end of the arm. As shown, in one or more embodiments, the arm may have rotation joint or other rotation mechanism 1089 to allow rotation of the end effector as shown by rotation arrow 1099. The rotation joint or mechanism combined with the horizontal and vertical members may give the robot at least 4-axis of movement. By way of example, once the carriage is in an appropriate position, the robot may rotate the end effector to achieve a desired orientation to engage with an item, and/or to achieve a desired orientation to place the item in a location.

In one or more embodiments, the end effector may include pincers, claws, jaws, hook-like structures or another gripper.

As shown in the illustration, in one aspect, the gripper may grip handle 447 having two magazines 222A/B attached.

Figure 10C:
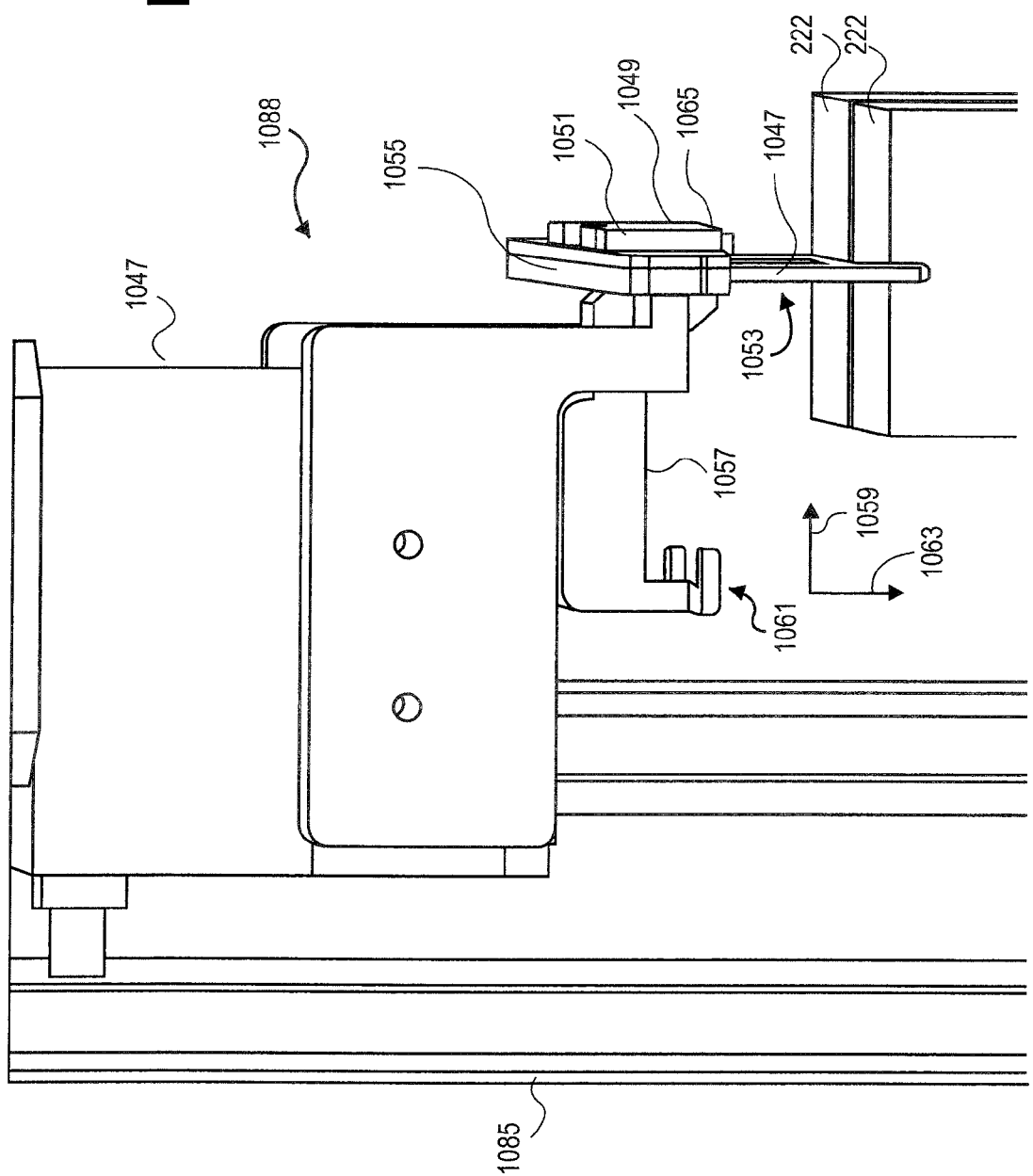
FIG. 10C is an expanded side, partial perspective, view of an embodiment of an end effector.

FIG. 10C is an expanded side partial perspective view of an embodiment of end effector 1088. The end effector is holding handle 1047 having magazines 222 attached. A portion of vertical member 1085 is also shown.

The end effector has end effector body 1047 and fixed jaw or other fixed member 1049. The fixed jaw has hook-like structure 1051. The hook-like structure may be introduced through an opening 1053 in handle 1047. Upper portion 1055 of the handle may rest on the hook-like structure. The handle may hang from the hook-like structure. In one or more embodiments, either the handle or the hook-like structure may include an alignment feature, such as, for example, a notch, groove, depression, or the like, to provide centering or other desired positioning of the handle on the hook-like structure.

The end effector also has movable jaw or other movable member 1057. The movable member may optionally move horizontally toward the hook-like structure in the direction of arrow 1059. The horizontal movement may continue until a lowermost portion 1061 of the movable jaw contacts the handle. This may help to stabilize the handle and/or reduce swaying or swinging during movement.

In one or more embodiments, the movable jaw may be used to remove the handle from the magazines. Initially, the handle having the magazines attached may hang from the hook-like structure as shown in FIG. 10C. In one particular embodiment, the magazines may be set down or placed into a conforming cavity or chamber, such as, for example, a rectangular shaped chamber having a floor and vertical sidewalls that is sized slightly larger than the two magazines. While the handle is pinched or held between fixed member 1049 and movable member 1057, the end effector may move away from the magazines in the reverse direction of arrow 1059 (to the left in the illustration). Since the magazines are in the conforming cavity, they may remain stationary while the handle is pulled in the reverse direction of arrow 1059. The handle may slide away from the magazines along grooves at the top of the magazines until it has been freed from the magazines.

In one or more embodiments, the movable jaw may be used to clamp a magazine after the handle has been removed. Lower portion 1065 of the fixed jaw may have a small flat surface where a magazine may rest against. The robot may move until the magazine is against or very near the small flat surface of the lower portion of the fixed jaw. The movable jaw may then move horizontally toward the magazine, in the direction of arrow 1059, until lowermost portion 1061 of the movable jaw contacts the magazine and applies a compression force on the magazines against the small flat surface of the lower portion of the fixed jaw. That is, the movable and fixed jaws may hold the magazine much like a C-clamp or G-clamp would. In one or more embodiments, lowermost portion 1061 of movable jaw 1057 may engage a magazine at the aforementioned grooves at the top of the magazine. (Recall that the handle slides away from the magazines along grooves at the top of the magazines.) Utilization of such grooves may help to improve gripping or engaging the magazine, but is not required.

This is just one example of a suitable integration unit and robot. Various other integration units and robots are contemplated, and will be apparent to those skilled in the art, and having the benefit of the present disclosure. As one example, another suitable robot is an articulated robot situated in front of, behind, or between the tissue processor and the embedding system, and having a sufficiently long and flexible arm to provide a work envelope encompassing the output of the tissue processor and the input of the embedding system. As another example, yet another suitable robot is an articulated robot situated at or on either the tissue processor or the embedding system, and having a sufficiently long and flexible arm to provide a work envelope encompassing the output of the tissue processor and the input of the embedding system. As yet another example, a still further suitable robot is an articulated robot coupled in a Gantry or Cartesian coordinate type robot configuration. Still other suitable robots are contemplated.

It is not required that an integration unit and/or a robot transfer magazines or other tissue holders all the way between a tissue processor and an embedding system. Some of the advantage may be achieved if the integration unit and/or the robot transfers the magazines part way between the tissue processor and the embedding system with another part of the transfer being performed manually.

Figure 11:
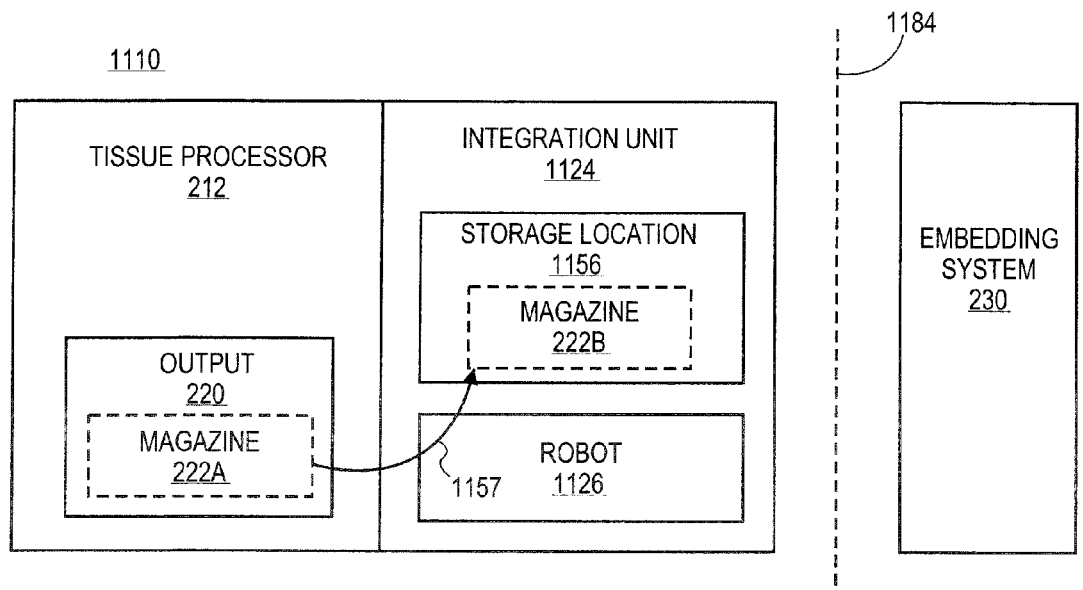
FIG. 11 is a block diagram of a fifth embodiment of an integrated tissue processing and embedding system, along with an embedding system.

FIG. 11 is a block diagram of a fifth embodiment of integrated tissue processing and embedding system 1110, which may be referred to simply as the integrated system, along with an embedding system 230. The integrated system includes tissue processor 212, and tissue processor/embedding system integration unit 1124, which for may be referred to simply as the integration unit. The tissue processor has output 220. The integration unit has storage location 1124 and robot 1126.

In one or more embodiments, integration unit 1124 and robot 1126 may be functionally or operatively coupled or connected with tissue processor 212, but not with embedding system 230. In one or more embodiments, as shown by arrow 1157, the robot may transfer magazine 222A from output 220 of the tissue processor to storage location 1156 of the integration unit as magazine 222B. Magazine 222B may be transferred from the storage location to the embedding system manually.

Figure 12:
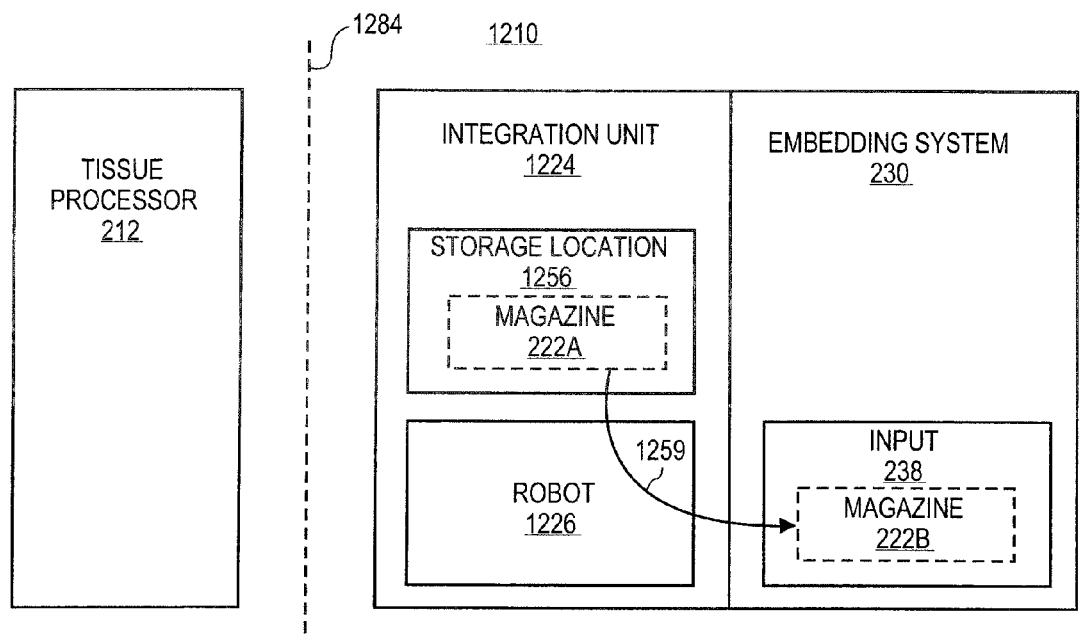
FIG. 12 is a block diagram of a sixth embodiment of an integrated tissue processing and embedding system, along with a tissue processor.

FIG. 12 is a block diagram of a sixth embodiment of integrated tissue processing and embedding system 1210, which may simply be referred to as the integrated system, along with a tissue processor 212. The integrated system includes embedding system 230, and tissue processor/embedding system integration unit 1224, which may simply be referred to as the integration unit. The integration unit has storage location 1256 and robot 1226. The embedding system has input 238.

In one or more embodiments, integration unit 1224 and robot 1226 may be functionally or operatively coupled or connected with embedding system 230, but not with tissue processor 212. In one or more embodiments, as shown by arrow 1259, the robot may transfer magazine 222A from storage location 1256 of the integration unit to input 238 of the embedding system as magazine 222B. Previously, magazine 222A may have been manually transferred from an output of the tissue processor to the storage location.

Aside from these differences, the tissue processors, embedding systems, and integration units, of FIGS. 11 and 12, and their components and functions, may optionally be similar to, or the same as, those of FIG. 2, and/or FIG. 6, and/or FIG. 8.

In one or more embodiments, an integration units described herein may optionally have a switch, button, or other mechanism to disable the integration unit, the robot, or both. This may allow operations to be performed manually, instead of by the robot. Switches, buttons, or other mechanisms may optionally be included, or retained, on the tissue processor and the embedding system to allow the output and input, respectively, to be opened and closed manually.

One or more embodiments pertain to a method of retrofitting or modifying an existing tissue processor and/or an existing embedding system to incorporate a tissue processor/embedding system integration unit and/or a robot as disclosed elsewhere herein. The method may include functionally or operatively coupling or connecting the integration unit and/or the robot with the tissue processor and/or the embedding system.

In one or more embodiments, the tissue processor and/or the embedding system may optionally be minimally modified so that an output of the tissue processor and/or an input of the embedding system may autonomously open and close.

One or more embodiments pertain to a kit having a tissue processor/embedding system integration unit and/or a robot, as described elsewhere herein, which may be used to retrofit or modify an existing tissue processor and/or an existing embedding system.

The kit may also include instructions, such as, for example installation or assembly instructions and/or use (e.g., programming) instructions.

FIG. 13 is a diagram of a seventh embodiment of an even more highly integrated tissue processing and embedding system 1310, which for convenience may simply be referred to as the integrated system. The integrated system includes input 1321, tissue processing mechanism 1314, embedding mechanism 1332, output 1339, and robot 1326. The input and the tissue processing mechanism may be similar to those found in conventional tissue processors. Likewise, the embedding mechanism and output may be similar to those found in conventional embedding systems.

The input may receive potentially grossed and fixated tissue within one or more tissue holders. The robot is functionally or operatively coupled to move or transfer the tissue within one or more tissue holders from the input to the tissue processing mechanism, from the tissue processing mechanism to the embedding mechanism, and from the embedding mechanism to the output. The embedded tissues may be removed from the output.

Integrated system 1310 has an even higher level of integration that the integrated systems shown in FIGS. 2, 6, 8, and 10. The input, the tissue processing mechanism, the embedding mechanism, the output, and the robot, may all be included within a housing or enclosure of a single system or instrument, instead of being separated instruments that have been integrated together for example by an intervening integration unit.

In the description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still co-operate or interact with each other.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate embodiments thereof. The scope of the invention is not to be determined by the specific examples provided above, but only by the claims below. In other instances, well-known components, mechanisms, structures, devices, and operations have been shown in block diagram form or without detail in order to avoid obscuring the understanding of the description.

It will also be appreciated, by one skilled in the art, that modifications may be made to the embodiments disclosed herein, such as, for example, to the sizes, configurations, forms, functions, and manner of operation, and use, of the components of the embodiments. All equivalent relationships to those illustrated in the drawings and described in the specification are encompassed within embodiments of the invention. Where considered appropriate, reference numerals or terminal portions of reference numerals have been repeated among the figures to indicate corresponding or analogous elements, which unless specified otherwise may optionally have similar characteristics.

Various operations and methods have been described. Some of the methods have been described in a basic form, but operations may optionally be added to and/or removed from the methods. The operations of the methods may also often optionally be performed in different order.

One or more embodiments of the invention may be provided as a program product or other article of manufacture that may include a machine-readable medium having stored thereon one or more instructions. The medium may provide instructions, which, if executed by a machine such as a robot or integration unit, may result in and/or cause the machine to perform one or more of the operations or methods disclosed herein. Suitable machines include, but are not limited to, robots, integration units, computer systems, laboratory equipment, and a wide variety of other machines, to name just a few examples. Representatively, the medium may include recordable mediums, such as, for example, floppy diskette, optical storage medium, optical disk, CD-ROM, magnetic disk, magneto-optical disk, read only memory (ROM), programmable ROM (PROM), erasable-and-programmable ROM (EPROM), electrically-erasable-and-programmable ROM (EEPROM), random access memory (RAM), static-RAM (SRAM), dynamic-RAM (DRAM), Flash memory, other types of memory, other machine-readable medium within programmable logic units used to control robots, and combinations thereof.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A tissue processor/embedding system integration unit, the tissue processor/embedding system integration unit comprising:
    a robot having an arm and an end effector coupled with the arm,
    wherein the robot is disposed between a tissue processor and an embedding system,
    wherein the robot has a work envelope,
    wherein the work envelope of the robot encompasses an output of the tissue processor,
    wherein the tissue processor is operable to remove water from tissue and infiltrate an embedding agent into the tissue,
    wherein the work envelope of the robot encompasses an input of the embedding system, wherein the embedding system is operable to embed the tissue from which the water has been removed and into which the embedding agent has been infiltrated in a block of an embedding medium, wherein the robot has movement in at least 4-axis; and instructions stored on a machine-readable medium to configure the robot to transfer a tissue holder having the tissue, from which the water has been removed and into which the embedding agent has been infiltrated, from the output of the tissue processor to the input of the embedding system.

2. An apparatus comprising:

a robot comprising a work envelope that encompasses a first location having a tissue holder and a different second location comprising an input of an embedding system, wherein the tissue holder is operable to contain at least one processed tissue from which water has been removed and an embedding agent has been infiltrated, wherein the robot is operable to transfer the tissue holder from the first location to the second location, and wherein the embedding system is operable to embed a processed tissue in a block of an embedding medium.

3. The apparatus of claim 2, further comprising instructions stored on a machine-readable medium to configure the robot to transfer the tissue holder from the location to the input of the embedding system.

4. The apparatus of claim 2, in which the robot is physically disposed between the embedding system and a tissue processor.

5. The apparatus of claim 2, in which the first location comprises an output of a tissue processor.

6. The apparatus of claim 2, further comprising a storage location serving as the location, in which the storage location is located outside of the embedding system and outside of a tissue processor.

7. The apparatus of claim 6, further comprising a heater to heat the storage location.

8. The apparatus of claim 7, in which the embedding agent comprise wax, and in which the heater is operable to heat the wax to a softening or melting point over a period ranging from 2 to 20 minutes.

9. The apparatus of claim 7, in which the heater comprises at least one of a heat lamp, a heating coil, a heating element, a resistance heater, a hot plate, a hot pad, one or more pipes having hot water or other heating fluid flowing through them, an electric heater, a radiative heater, a space heater, and a combination thereof.

10. The apparatus of claim 6, in which the robot is configured to transfer the tissue holder from an output of a tissue processor to the storage location before transferring the tissue holder to the input of the embedding system.

11. The apparatus of claim 2, in which the work envelope encompasses an empty tissue holder output of the embedding system, and in which the robot is configured to move an empty tissue holder away from the empty tissue holder output.

12. The apparatus of claim 11, further comprising a cleaning mechanism to clean the empty tissue holder, in which the robot is configured to move the empty tissue holder to the cleaning mechanism.

13. The apparatus of claim 12, in which the cleaning mechanism is operable to remove wax from the empty tissue holder, and in which the cleaning mechanism comprises at least one of a spray of heated and pressurized water, a bath of a dewaxing composition, a shower of a dewaxing composition, a heated water bath, a heated water shower, a steam treatment, a scrubbing mechanism, and a combination thereof.

14. The apparatus of claim 12, wherein the cleaning mechanism comprises a spray of heated and pressurized water, in which the heated water has a temperature ranging from 70° C. to 100° C., and in which the water used to form the spray has a pressure ranging from several hundred to several thousand pounds per square inch (PSI).

15. The apparatus of claim 2, in which the robot has at least 4-axis.

16. The apparatus of claim 2, in which the robot comprises:

a horizontal member leading from the embedding system to a tissue processor;

a carriage moveably coupled with the horizontal member; and an arm having an end effector coupled with the carriage.

17. The apparatus of claim 16, further comprising a vertical member coupled with and leading downward from the horizontal member, in which the carriage is also moveably coupled with the vertical member, and in which the arm comprises a rotation mechanism.

18. An integrated tissue processor and embedding system, the integrated tissue processor and embedding system comprising:

an input to allow a tissue holder operable to contain a tissue to be input;

a tissue processing mechanism, wherein the tissue processing mechanism is operable to process tissue to remove water from a tissue and infiltrate an embedding agent into the tissue;

an embedding mechanism, wherein the embedding mechanism is operable to embed processed tissue in a block of an embedding medium;

an output to allow the block embedded tissue to be output;

a robot; and instructions stored on a machine-readable medium to configure the robot to transfer processed tissue from the tissue processing mechanism to the embedding mechanism.

* * * * *